(12) United States Patent
Murakita

(10) Patent No.: US 12,178,402 B2
(45) Date of Patent: Dec. 31, 2024

(54) IMAGE PROCESSING SYSTEM, IMAGE PROCESSING DEVICE, AND IMAGE PROCESSING METHOD

(71) Applicant: Sony Group Corporation, Tokyo (JP)

(72) Inventor: Masashi Murakita, Tokyo (JP)

(73) Assignee: Sony Group Corporation, Tokyo (JP)

( * ) Notice: Subject to any disclaimer, the term of this patent is extended or adjusted under 35 U.S.C. 154(b) by 310 days.

(21) Appl. No.: 17/441,294

(22) PCT Filed: Mar. 27, 2020

(86) PCT No.: PCT/JP2020/014119
§ 371 (c)(1),
(2) Date: Sep. 21, 2021

(87) PCT Pub. No.: WO2020/203810
PCT Pub. Date: Oct. 8, 2020

(65) Prior Publication Data
US 2022/0142454 A1    May 12, 2022

(30) Foreign Application Priority Data

Mar. 29, 2019 (JP) ................. 2019-065381

(51) Int. Cl.
*G06T 7/62* (2017.01)
*A61B 1/00* (2006.01)
(Continued)

(52) U.S. Cl.
CPC .... *A61B 1/00188* (2013.01); *A61B 1/000094* (2022.02); *A61B 1/000095* (2022.02);
(Continued)

(58) Field of Classification Search
CPC .......... A61B 1/00188; A61B 1/000094; A61B 1/000095; A61B 1/045; G06T 7/0014;
(Continued)

(56) References Cited

U.S. PATENT DOCUMENTS

2007/0132839 A1    6/2007  Pang et al.
2010/0048993 A1    2/2010  Shidara
(Continued)

FOREIGN PATENT DOCUMENTS

CN    105476598 A    4/2016
JP    2004-33487 A   2/2004
(Continued)

OTHER PUBLICATIONS

International Search Report and Written Opinion mailed on Jun. 19, 2020, received for PCT Application PCT/JP2020/014119, Filed on Mar. 27, 2020, 15 pages.

*Primary Examiner* — Michael E Teitelbaum
(74) *Attorney, Agent, or Firm* — XSENSUS LLP

(57) ABSTRACT

An endoscope system includes circuitry configured to set a plurality of evaluation areas in an endoscope image captured by an image sensor via a scope, adjacent ones of the plurality of evaluation areas being spatially separated from one another, calculate an evaluation value for each of the plurality of evaluation areas, compare an evaluation value of the
(Continued)

plurality of evaluation areas, and adjust an image processing on the endoscope image in accordance with a result of the comparison.

19 Claims, 18 Drawing Sheets

(51) Int. Cl.
| | | |
|---|---|---|
| *A61B 1/045* | (2006.01) | |
| *G06T 7/00* | (2017.01) | |
| *G06T 7/66* | (2017.01) | |
| *G06T 7/70* | (2017.01) | |
| *H04N 23/50* | (2023.01) | |
| *H04N 23/56* | (2023.01) | |
| *H04N 23/71* | (2023.01) | |

(52) U.S. Cl.
CPC ............ *A61B 1/045* (2013.01); *G06T 7/0014* (2013.01); *G06T 7/62* (2017.01); *G06T 7/66* (2017.01); *G06T 7/70* (2017.01); *H04N 23/71* (2023.01); *G06T 2207/10068* (2013.01); *G06T 2207/30004* (2013.01); *H04N 23/555* (2023.01); *H04N 23/56* (2023.01)

(58) Field of Classification Search
CPC .... G06T 7/62; G06T 7/66; G06T 7/70; G06T 2207/10068; G06T 2207/30004; H04N 23/71; H04N 23/555; H04N 23/56
See application file for complete search history.

(56) References Cited

U.S. PATENT DOCUMENTS

| | | | |
|---|---|---|---|
| 2017/0296032 A1 | 10/2017 | Li | |
| 2018/0242828 A1 | 8/2018 | Shiga et al. | |
| 2019/0053693 A1 | 2/2019 | Koiso et al. | |
| 2020/0077869 A1* | 3/2020 | Ida | G06T 5/005 |

FOREIGN PATENT DOCUMENTS

| | | |
|---|---|---|
| JP | 2009519764 A | 5/2009 |
| JP | 2010046276 A | 3/2010 |
| JP | 2016163609 A | 9/2016 |
| JP | 2019033917 A | 3/2019 |
| WO | 2014/208224 A1 | 12/2014 |
| WO | WO-2017072950 A | 5/2017 |
| WO | WO-2018235389 A | 12/2018 |
| WO | 2019/181629 A1 | 9/2019 |

\* cited by examiner

IMAGE PROCESSING SYSTEM, IMAGE PROCESSING DEVICE, AND IMAGE PROCESSING METHOD

CROSS-REFERENCE TO RELATED APPLICATIONS

The present application is based on PCT filing PCT/JP2020/014119, filed Mar. 27, 2020, which claims priority to JP 2019-065381, filed Mar. 29, 2019, the entire contents of each are incorporated herein by reference.

TECHNICAL FIELD

The present disclosure relates to an image processing system, an image processing device, and an image processing method, and more particularly, to an image processing system, an image processing device, and an image processing method enabled to determine a type of a scope with a less amount of calculation.

BACKGROUND ART

In general, a surgical endoscope uses a camera head to which a scope is connected, and the scope is inserted into a patient, whereby a surgical field is observed.

The scope is removable and a scope to be used is selected from a plurality of types of scopes. Mechanical vignetting and other imaging properties differ depending on the type of the scope. Since subsequent image processing is to be adjusted in accordance with scope type, a method for determining the scope type is needed.

For example, PTL 1 discloses a method for determining the scope type.

CITATION LIST

Patent Literature

PTL 1: JP 2004-33487A

SUMMARY OF INVENTION

Technical Problem

However, as disclosed in PTL 1, determining the scope type requires detection of all straight edges in the image, which uses a large amount of calculation. A method has, therefore, been demanded for determining the scope type with less calculation.

The present disclosure has been made in view of such a situation and enables determination of the scope type with a smaller amount of calculation.

Solution to Problem

An image processing system of one aspect of the present disclosure is an image processing system including a control unit that sets a plurality of evaluation frames arranged at a predetermined interval for an endoscopic image captured by using a scope, calculates evaluation values regarding the respective plurality of evaluation frames set, and estimates a type of the scope on the basis of a relationship between the evaluation values calculated.

An image processing device of one aspect of the present disclosure is an image processing device including a control unit that sets a plurality of evaluation frames arranged at a predetermined interval for an endoscopic image captured by using a scope, calculates evaluation values regarding the respective plurality of evaluation frames set, and performs signal processing corresponding to a type of the scope on the basis of a relationship between the evaluation values calculated.

An image processing method of one aspect of the present disclosure is an image processing method including, by an image processing device, setting a plurality of evaluation frames arranged at a predetermined interval for an endoscopic image captured by using a scope, calculating evaluation values regarding the respective plurality of evaluation frames set, and performing signal processing corresponding to a type of the scope on the basis of a relationship between the evaluation values calculated.

In the image processing system, the image processing device, and the image processing method of one aspect of the present disclosure, a plurality of evaluation frames arranged at a predetermined interval is set for an endoscopic image captured by using a scope, evaluation values regarding the respective plurality of evaluation frames set are calculated, and a type of the scope is estimated on the basis of a relationship between the evaluation values calculated.

Note that, the image processing device of one aspect of the present disclosure may be an independent device or an internal block constituting one device.

DESCRIPTION OF EMBODIMENTS

Hereinafter, embodiments of a technology (the present technology) according to the present disclosure will be described with reference to the drawings. Note that, the description will be made in the following order.
1. Embodiment of the present technology
2. Modifications
3. Configuration of computer

1. Embodiment of the Present Technology (Overview of System)

Figure 1:
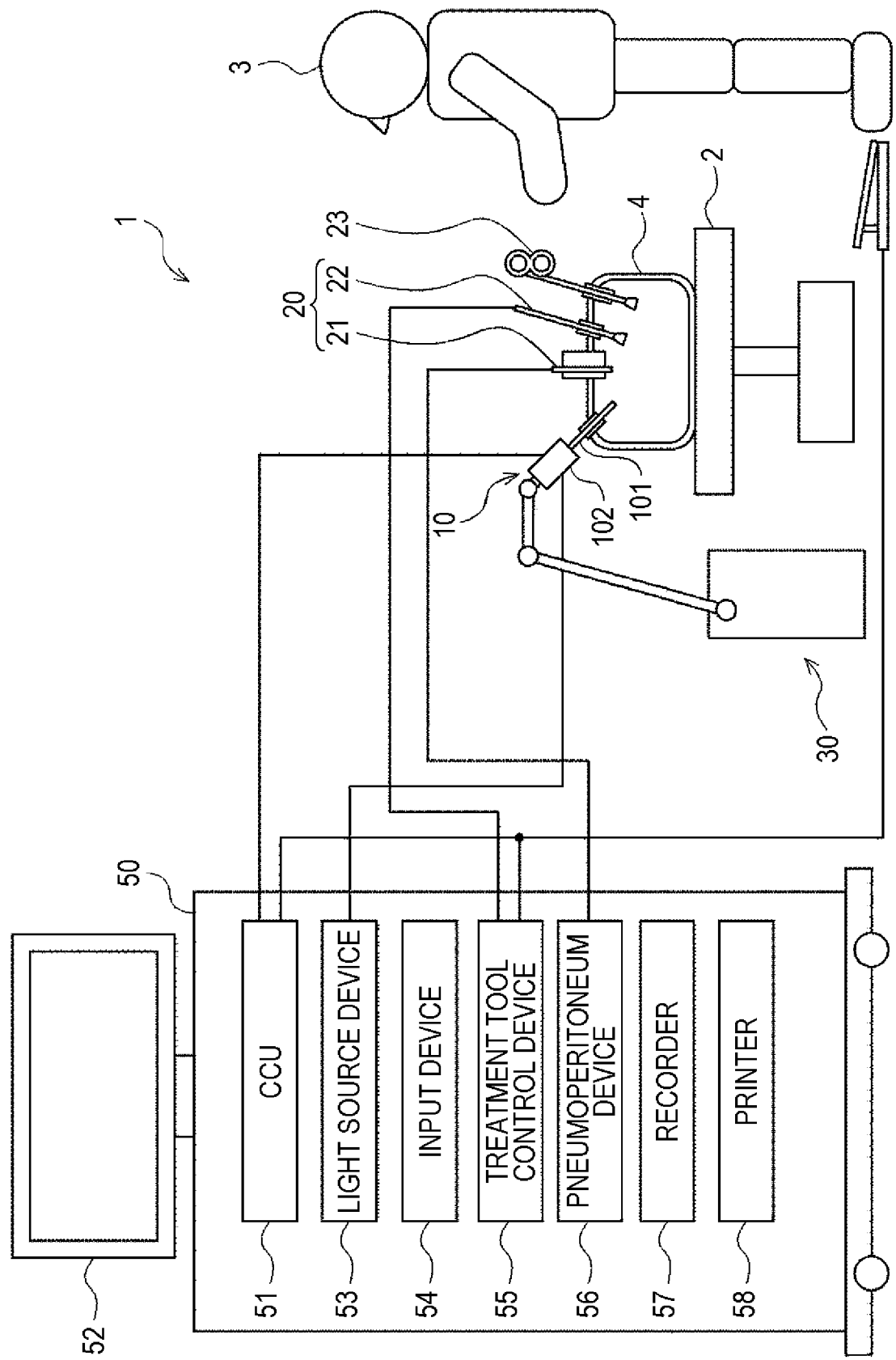
FIG. 1 is a diagram illustrating an example of a schematic configuration of an image processing system to which a technology according to the present disclosure is applied.

First, an overview will be described of a system to which the technology according to the present disclosure can be applied. FIG. 1 illustrates an example of a schematic configuration of an image processing system to which the technology according to the present disclosure is applied.

FIG. 1 illustrates a state in which an operator (surgeon) 3 is performing surgery on a patient 4 on a patient bed 2 by using an endoscopic surgical system 1. In FIG. 1, the endoscopic surgical system 1 includes: an endoscope 10; other surgical tools 20 such as a pneumoperitoneum tube 21, an energy treatment tool 22, and forceps 23; a support arm device 30 that supports the endoscope 10; and a cart 50 on which various devices for endoscopic surgery are mounted.

The endoscope 10 includes a scope 101 of which an area of a predetermined length from the distal end is inserted into the body cavity of the patient 4, and a camera head 102 connected to the proximal end of the scope 101. Note that, FIG. 1 illustrates the endoscope 10 configured as a so-called rigid scope including a rigid scope 101, but the endoscope 10 may be configured as a so-called flexible scope including a flexible lens barrel.

At the distal end of the scope 101, an opening is provided into which an objective lens is fitted. A light source device 53 is connected to the endoscope 10, and light (irradiation light) generated by the light source device 53 is guided to the distal end of the lens barrel by a light guide extending inside the scope 101, and the light is emitted toward an observation target in the body cavity of the patient 4 via the objective lens. Note that, the endoscope 10 may be a forward-viewing endoscope, an oblique-viewing endoscope, or a side-viewing endoscope.

An optical system and an imaging element are provided inside the camera head 102, and reflected light (observation light) from the observation target is focused on the imaging element by the optical system. The imaging element photoelectrically converts the observation light to generate an image signal corresponding to a subject image. The image signal is transmitted as RAW data (RAW image) to a camera control unit (CCU) 51.

The CCU 51 includes a processor, for example, a central processing unit (CPU), a graphics processing unit (GPU), or the like, and comprehensively controls operation of the endoscope 10 and a display device 52. Moreover, the CCU 51 receives the image signal from the camera head 102, and performs, on the image signal, various types of image processing for displaying an observation image (display image) based on the image signal, for example, development processing (demosaic processing), and the like.

The display device 52 displays the display image based on the image signal subjected to the image processing by the CCU 51 in accordance with the control from the CCU 51.

The light source device 53 includes a light source, for example, a light emitting diode (LED) or the like, and supplies irradiation light for imaging a surgical portion or the like to the endoscope 10.

An input device 54 is an input interface to the endoscopic surgical system 1. A user can input various types of information and instructions to the endoscopic surgical system 1 via the input device 54. For example, the user inputs an instruction or the like to change imaging conditions (type of irradiation light, magnification, focal length, and the like) for the endoscope 10.

A treatment tool control device 55 controls driving of the energy treatment tool 22 for cauterization of tissue, incision, sealing of blood vessels, or the like. A pneumoperitoneum device 56 injects a gas into the body cavity via the pneumoperitoneum tube 21 to inflate the body cavity of the patient 4, for the purpose of securing a visual field by the endoscope 10 and securing a working space of the operator.

A recorder 57 is a device enabled to record various types of information regarding surgery. A printer 58 is a device enabled to print various types of information regarding surgery in various formats such as text, image, graph, and the like.

(Detailed Configuration of Endoscope)

Figure 2:
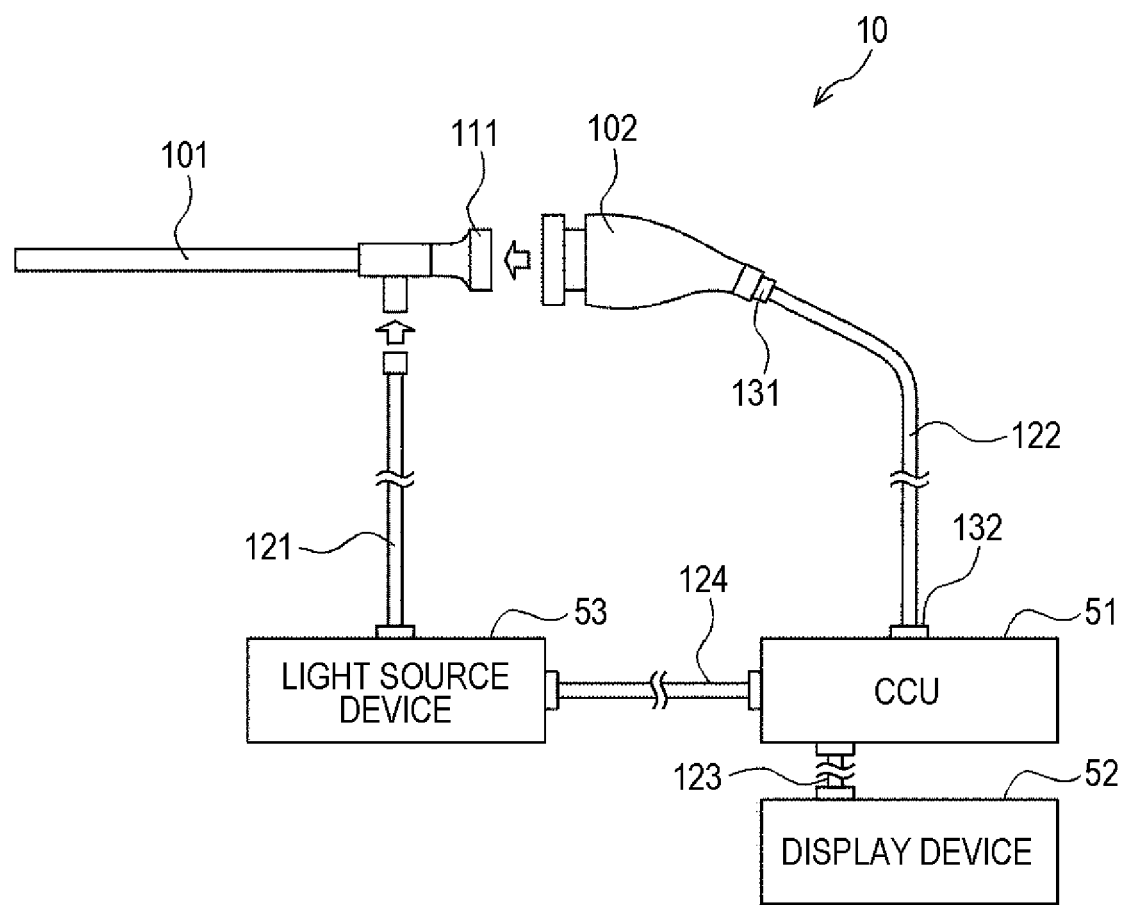
FIG. 2 is a diagram illustrating an example of a configuration of an endoscope.

FIG. 2 illustrates an example of a detailed configuration of an endoscope 10 of FIG. 1.

In FIG. 2, the endoscope 10 includes the scope 101 and the camera head 102. Furthermore, in the endoscope 10, the scope 101 is connected to the light source device 53 via a light guide 121, and the camera head 102 is connected to the CCU 51 via a transmission cable 122. Moreover, the CCU 51 is connected to the display device 52 via a transmission cable 123, and the light source device 53 via a transmission cable 124.

The scope 101 is configured as a rigid scope. In other words, the scope 101 is an insertion portion (lens barrel) that is rigid or at least partially soft and has an elongated shape, and is inserted into the body cavity of the patient 4. In the scope 101, an optical system is provided that is configured by using one or a plurality of lenses and focuses a subject image.

The light source device 53 is connected to one end of the light guide 121, and supplies irradiation light for illuminating the inside of the body cavity to one end of the light guide 121 in accordance with the control of the CCU 51. One end of the light guide 121 is detachably connected to the light source device 53, and the other end is detachably connected to the scope 101.

Then, the light guide 121 transmits the irradiation light supplied from the light source device 53 from one end to the other end, and supplies the light to the scope 101. The irradiation light supplied to the scope 101 is emitted from the distal end of the scope 101, and is emitted into the body cavity. The observation light (subject image) emitted into the body cavity and reflected in the body cavity is focused by the optical system in the scope 101.

The camera head 102 is detachably connected to the proximal end (an eyepiece 111) of the scope 101. Then, the camera head 102 captures the observation light (subject image) focused by the scope 101 in accordance with the control of the CCU 51, and outputs an image signal (RAW data) obtained as a result. The image signal is, for example, an image signal corresponding to 4K resolution (for example, 3840×2160 pixels). Note that, a detailed configuration of the camera head 102 will be described later with reference to FIG. 3.

One end of the transmission cable 122 is detachably connected to the camera head 102 via a connector 131, and the other end is detachably connected to the CCU 51 via a connector 132. Then, the transmission cable 122 transmits the image signal and the like output from the camera head 102 to the CCU 51, and transmits each of a control signal, a synchronization signal, power, and the like output from the CCU 51 to the camera head 102.

Note that, in the transmission of the image signal and the like from the camera head 102 to the CCU 51 via the transmission cable 122, the image signal and the like may be transmitted as an optical signal, or may be transmitted as an electrical signal. The same applies to the control signal, synchronization signal, and clock from the CCU 51 to the camera head 102 via the transmission cable 122. Furthermore, communication between the camera head 102 and the CCU 51 is not limited to wired communication using the transmission cable 122, and wireless communication may be performed conforming to a predetermined communication scheme.

The display device 52 displays the display image based on the image signal from the CCU 51 in accordance with the control from the CCU 51, and outputs sound depending on the control signal from the CCU 51.

One end of the transmission cable 123 is detachably connected to the display device 52, and the other end is detachably connected to the CCU 51. Then, the transmission cable 123 transmits the image signal processed by the CCU 51 and the control signal output from the CCU 51 to the display device 52.

The CCU 51 includes a CPU and the like, and comprehensively controls operations of the light source device 53, the camera head 102, and the display device 52. Note that, a detailed configuration of the CCU 51 will be described later with reference to FIG. 3.

One end of the transmission cable 124 is detachably connected to the light source device 53, and the other end is detachably connected to the CCU 51. Then, the transmission cable 124 transmits the control signal from the CCU 51 to the light source device 53.

(Detailed Configuration of Camera Head and CCU)

Figure 3:
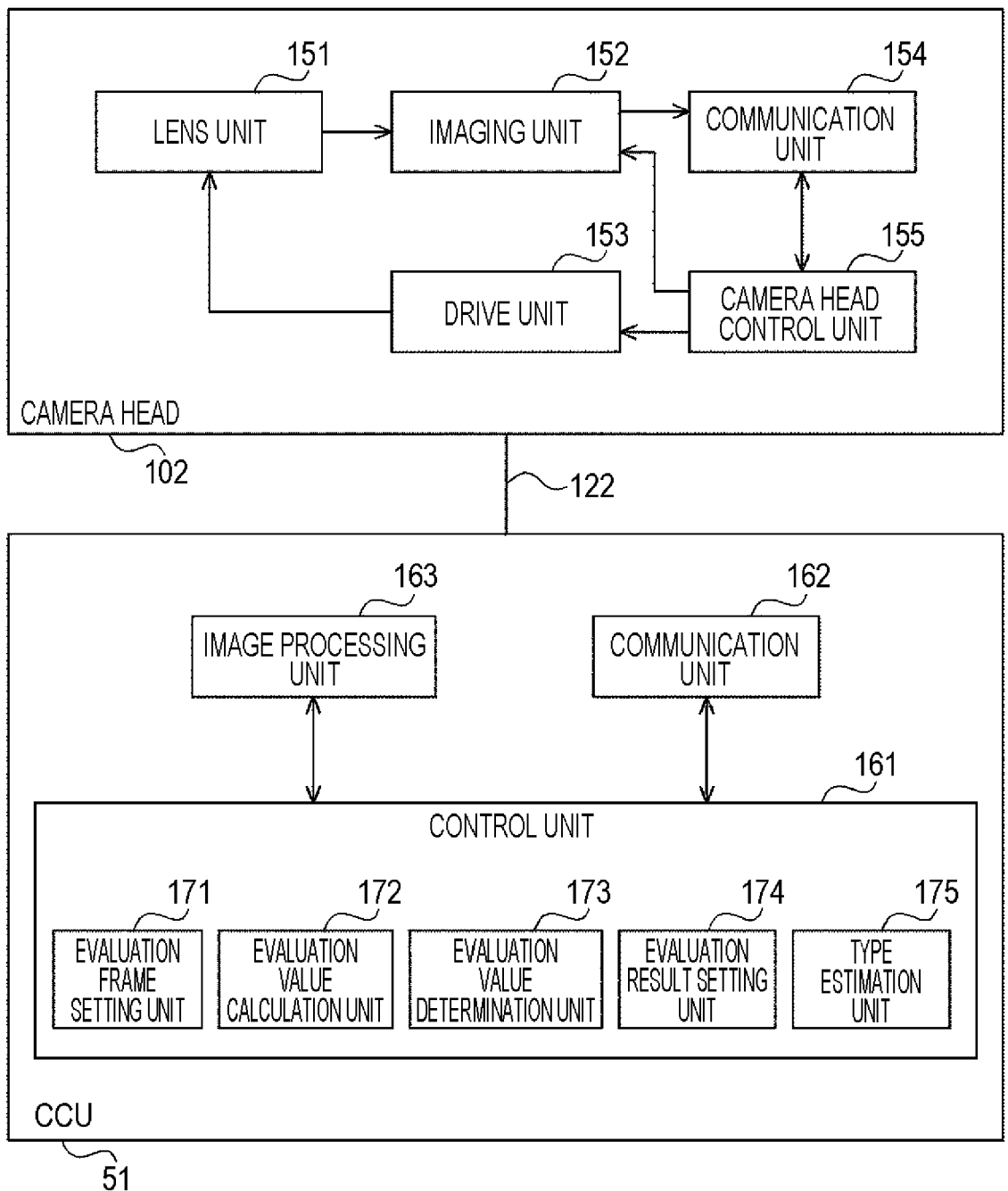
FIG. 3 is a block diagram illustrating an example of a functional configuration of a camera head and a CCU.

FIG. 3 is a block diagram illustrating an example of a functional configuration of the camera head 102 and the CCU 51 illustrated in FIGS. 1 and 2.

The camera head 102 includes a lens unit 151, an imaging unit 152, a drive unit 153, a communication unit 154, and a camera head control unit 155. The camera head 102 and the CCU 51 are communicably connected to each other by the transmission cable 122.

The lens unit 151 is an optical system provided at a connection portion with the scope 101. The observation light taken in from the distal end of the scope 101 is guided to the camera head 102 and is incident on the lens unit 151. The lens unit 151 includes a plurality of lenses, e.g., a zoom lens, a focus lens, and the like.

The imaging unit 152 includes an imaging element, e.g., a complementary metal oxide semiconductor (CMOS) image sensor, a charge coupled device (CCD) image sensor, or the like. The imaging element constituting the imaging unit 152 may be one (so-called single plate type) element, or a plurality of (so-called multiple plate type) elements. In a case where the imaging unit 152 includes the multiple plate type, for example, image signals respectively corresponding to R, G, and B may be generated by respective imaging elements, and a color image may be obtained by synthesizing the image signals.

Alternatively, the imaging unit 152 may include a pair of imaging elements for respectively acquiring right-eye and left-eye image signals corresponding to three-dimensional (3D) display. The 3D display is performed, whereby the operator 3 can determine the depth of living tissue in a surgical portion more accurately. Note that, in a case where the imaging unit 152 includes the multiple plate type, a plurality of systems of the lens units 151 can be provided corresponding to respective imaging elements.

Furthermore, the imaging unit 152 does not necessarily have to be provided in the camera head 102. For example, the imaging unit 152 may be provided immediately after the objective lens, inside the scope 101.

The drive unit 153 includes an actuator and the like, and moves one or more of the plurality of lenses included in the lens unit 151 by a predetermined distance along the optical axis by control from the camera head control unit 155. As a result, magnification and focus of an image captured by the imaging unit 152 can be adjusted as appropriate.

The communication unit 154 includes a communication device for transmitting/receiving various types of information to/from the CCU 51. The communication unit 154 transmits the image signal obtained from the imaging unit 152 as RAW data to the CCU 51 via the transmission cable 122.

Furthermore, the communication unit 154 receives a control signal for controlling drive of the camera head 102 from the CCU 51, and supplies the control signal to the camera head control unit 155. The control signal includes, for example, information regarding imaging conditions such as information specifying a frame rate of the image, information specifying an exposure value at the time of imaging, or information specifying magnification and focus of the image.

Note that, the imaging conditions such as the frame rate, exposure value, magnification, and focus may be specified as appropriate by the user, or automatically set by the control unit 161 of the CCU 51 on the basis of the image signal acquired. That is, in the latter case, so-called auto exposure (AE), auto-focus (AF), and auto white balance (AWB) functions are installed in the endoscope 10.

The camera head control unit 155 controls the drive of the camera head 102 on the basis of the control signal from the CCU 51 received via the communication unit 154.

The CCU 51 is an image processing device including the control unit 161, a communication unit 162, and an image processing unit 163.

The control unit 161 performs various types of control regarding imaging of a surgical portion or the like by the endoscope 10 and display of an endoscopic image (medical image) obtained by the imaging of the surgical portion or the like. For example, the control unit 161 generates the control signal for controlling the drive of the camera head 102.

Furthermore, the control unit 161 causes the display device 52 to display a display image (endoscopic image) of the surgical portion or the like on the basis of the image signal subjected to the image processing by the image processing unit 163. At this time, the control unit 161 may recognize various objects in the image by using various image recognition technologies.

For example, the control unit 161 detects color, a shape of an edge, and the like of the object included in the image, thereby being able to recognize a surgical tool such as forceps, a specific body part, bleeding, mist at the time of using the energy treatment tool 22, or the like. When causing the display device 52 to display the image, the control unit 161 may cause various types of surgery assistance information to be superimposed and displayed on the image of the surgical portion by using the recognition result. The surgery assistance information is superimposed and displayed, and presented to the operator 3, whereby a burden on the operator 3 can be reduced, and the operator 3 can reliably perform surgery.

The communication unit 162 includes a communication device for transmitting/receiving various types of information to/from the camera head 102. The communication unit 162 receives the image signal transmitted from the camera head 102 via the transmission cable 122.

Furthermore, the communication unit 162 transmits the control signal for controlling the drive of the camera head 102 to the camera head 102. The image signal and the control signal can be transmitted by electrical communication, optical communication, or the like.

The image processing unit 163 performs various types of image processing on the image signal including RAW data transmitted from the camera head 102.

Furthermore, the control unit 161 includes an evaluation frame setting unit 171, an evaluation value calculation unit 172, an evaluation value determination unit 173, an evaluation result setting unit 174, and a type estimation unit 175.

The evaluation frame setting unit 171 sets a plurality of evaluation frames or evaluation areas arranged at a predetermined interval for an endoscopic image (RAW image) corresponding to the image signal (RAW data). Here, the evaluation frames each are an area arbitrarily set for an area (area of the RAW image) corresponding to an imaging surface of an imaging element having a predetermined array pattern, e.g., a Bayer array, and each evaluation frame may be, e.g., a frame for acquiring an evaluation value such as information regarding brightness (luminance information).

The evaluation value calculation unit 172 calculates evaluation values regarding the respective plurality of evaluation frames set by the evaluation frame setting unit 171. As the evaluation values, for example, luminance information (luminance value) in each evaluation frame is calculated. Note that, the evaluation value is not limited to the luminance value, and may be, for example, a quantitative value (for example, a feature value such as an edge amount or a black area amount) representing an edge, a black area, or the like included in the evaluation frame.

The evaluation value determination unit 173 determines a relationship (correlation) between the evaluation values for the respective plurality of evaluation frames calculated by the evaluation value calculation unit 172. Here, for example, a relationship is determined between evaluation values respectively corresponding to evaluation frames arranged adjacently or at a constant interval.

The evaluation result setting unit 174 performs setting regarding an evaluation result depending on the relationship between the evaluation values determined by the evaluation value determination unit 173.

The type estimation unit 175 estimates a scope type of the scope 101 of the endoscope 10 on the basis of the relationship between the evaluation values determined by the evaluation value determination unit 173. For example, from the relationship between the evaluation values, the scope type of the scope 101 can be estimated by detecting a mask edge as a boundary between a black area (hereinafter also referred to as a mask area) in which mechanical vignetting occurs due to the scope 101 and an area of a subject image (an effective area in which mechanical vignetting does not occur).

The type of the scope 101 is defined, e.g., a diameter or a shape of the scope 101. Since the size of the area of the subject image is determined by the type of the scope 101, if a correlation between the size of the area of the subject image and the type of the scope 101 is recorded in advance, the type of the scope 101 can be obtained from the size of the subject image.

Note that, there is a case where the area of the subject image is not circular, but is rectangular or octagonal, for example, depending on the type of the scope 101. In a case where the area is not circular, for example, the length of a straight line that maximizes the length in the vertical or horizontal direction of the area of the subject image may be used as the diameter of the scope 101. Furthermore, the center position of the scope 101 may be estimated together with the diameter of the scope 101.

By the way, as described above, in the endoscope 10, the scope 101 connected to the camera head 102 is inserted into the body cavity of the patient 4, whereby the surgical field is observed by the operator 3.

Figure 4:
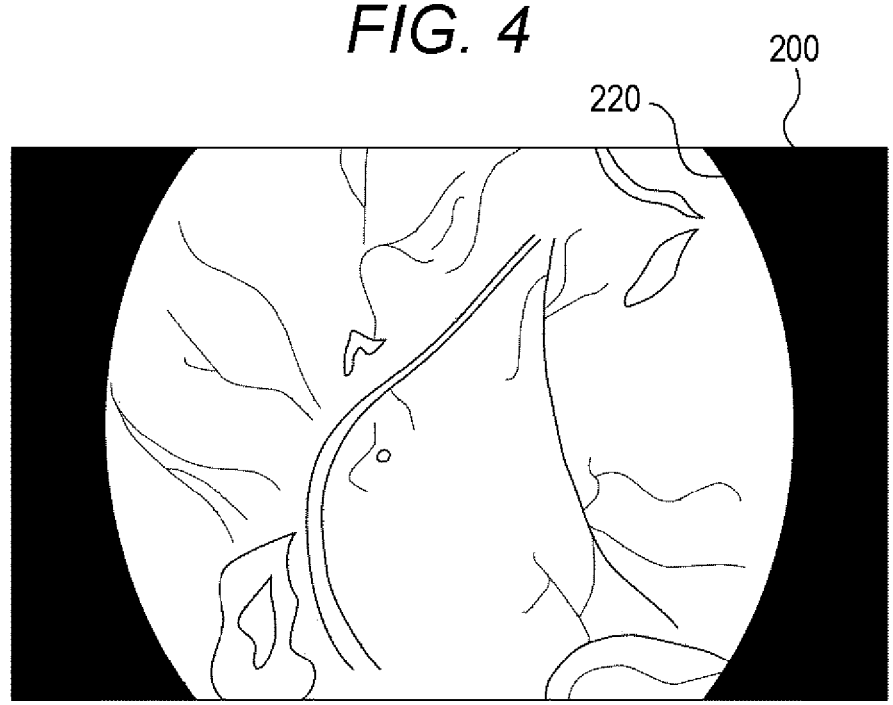
FIG. 4 is a diagram illustrating a first example of an endoscopic image.

For example, FIG. 4 illustrates an example of an endoscopic image 200 corresponding to an image signal obtained by imaging a subject image focused by the scope 101 by the camera head 102. In the endoscopic image 200, left and right black areas each represent a mask area in which mechanical vignetting occurs, and a boundary between an area of the subject image and the mask area (black area) is a mask edge 220.

In other words, in the endoscope 10, the scope 101 having an elongated shape is attached, and shapes do not match each other of the subject image focused by the scope 101 and the imaging surface of the imaging element of (the imaging unit 152 of) the camera head 102, so that mechanical vignetting occurs due to the scope 101.

Figure 5:
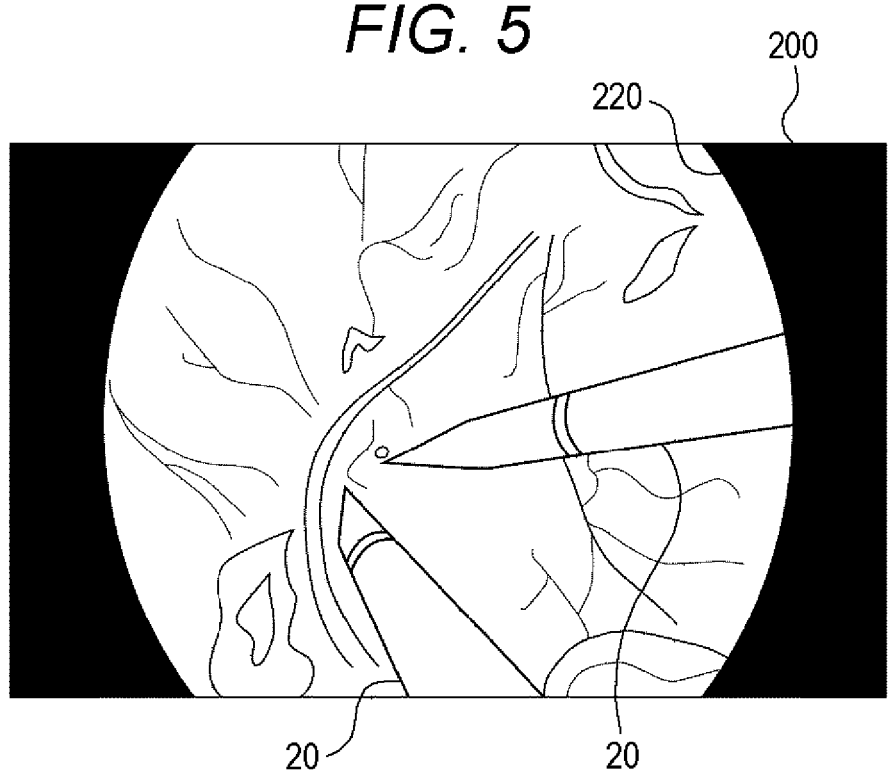
FIG. 5 is a diagram illustrating a second example of the endoscopic image.

Note that, the endoscopic image 200 is displayed by the display device 52 as a display image by being subjected to various types of image processing. For example, as illustrated in FIG. 5, the operator 3 can perform a treatment such as excising an affected part by using the surgical tool 20 such as the energy treatment tool 22 while viewing the display image in real time.

Here, in the endoscope 10, the scope 101 is removable, and the scope 101 to be used is selected from a plurality of types of scopes. At this time, mechanical vignetting and optical imaging properties differ depending on the scope type of the scope 101 used. As subsequent image processing is adjusted depending on the scope type of the scope 101, so that a method for determining scope the type of the scope 101 used is needed.

For example, signal processing regarding AF, AE, or the like is performed on the area of the subject image, and various problems arise when focusing or exposing is performed including the mask area, so that the scope type of the scope 101 used needs to be determined.

As described above, PTL 1 requires detection of all straight edges in the image to determine the scope type, so that the amount of calculation increases. A method has, therefore, been demanded for determining the type of the scope 101 used with a smaller amount of calculation.

In the present technology, a method is therefore devised for solving such a problem and determining the type of the scope 101 used, with a smaller amount of calculation. Hereinafter, details of the present technology will be described with reference to the drawings.

Note that, in (the CCU 51 of) the endoscopic surgical system 1, since first processing to fifth processing and determination processing are executed as processing for determining the type of the scope 101 used, these types of processing will be described in order. Furthermore, also in the following description, an image corresponding to the imaging surface of the imaging element of the camera head 102 will be referred to as an endoscopic image.
(Flow of First Processing)

First, a flow of the first processing executed by the CCU 51 will be described with reference to a flowchart of FIG. 6.

In step S10, the evaluation frame setting unit 171 sets a plurality of evaluation frames for an image (RAW image) corresponding to an image signal from the camera head 102. In the setting of the evaluation frames, as illustrated in FIG. 7, evaluation frames 210 are respectively provided at the central portion and the four peripheral corners of the endoscopic image 200.

Specifically, in the endoscopic image 200, a rectangular evaluation frame 210-0 (hereinafter also simply referred to as a frame 0) is provided at the central portion, and rectangular evaluation frames of an evaluation frame 210-1, an evaluation frame 210-2, an evaluation frame 210-3, and an evaluation frame 210-4 (hereinafter also simply referred to as a frame 1, a frame 2, a frame 3, and a frame 4) are provided at the four corners of the upper left, lower left, upper right, and lower right.

However, the sizes of the rectangles of the evaluation frames 210-1 to 210-4 are smaller than the size of the rectangle of the evaluation frame 210-0.

Figure 7:
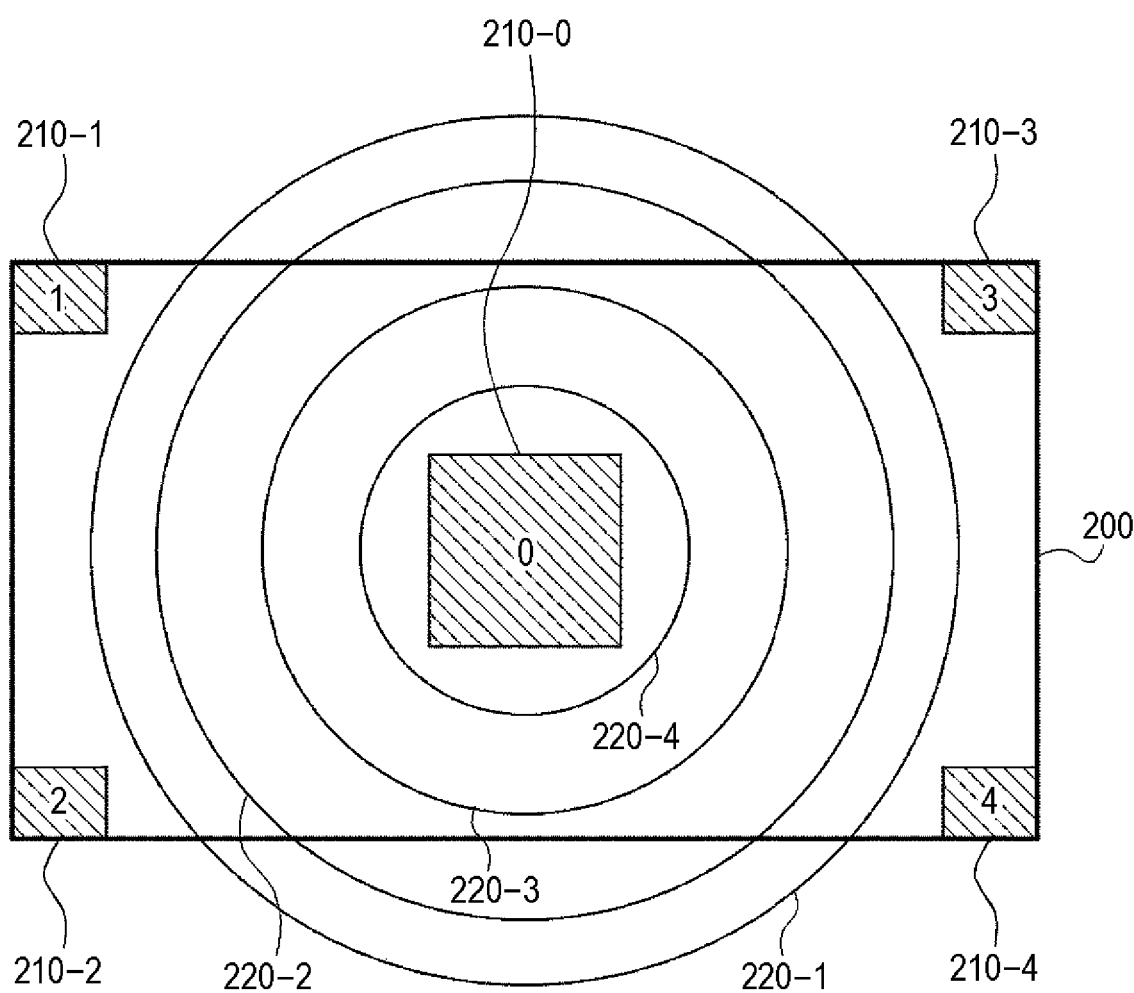
FIG. 7 is a diagram illustrating an example of a plurality of evaluation frames set in the first processing.

Furthermore, in FIG. 7, four circles having different diameters centered on the approximate center of gravity are indicated to be superimposed on the endoscopic image 200, and these circles respectively correspond to the mask edges 220 each being a boundary between the subject image area and the mask area.

In other words, the diameter of the scope 101 used in the endoscope 10 corresponds to the mask edge 220 in the endoscopic image 200, and since positions where the mask edges 220 are assumed to be detected in the endoscopic image 200 are known in advance on the design, here, the evaluation frames 210-0 to 210-4 are provided to determine whether or not the mask area is included.

Note that, in the following description, four types are assumed as the type of the scope 101 used, and it is assumed that, as a mask type of each mask edge 220, "TYPE1" is assigned for a mask edge 220-1, "TYPE2" is assigned for a mask edge 220-2, "TYPE3" is assigned for a mask edge 220-3, and "TYPE4" is assigned for a mask edge 220-4.

Figure 6:
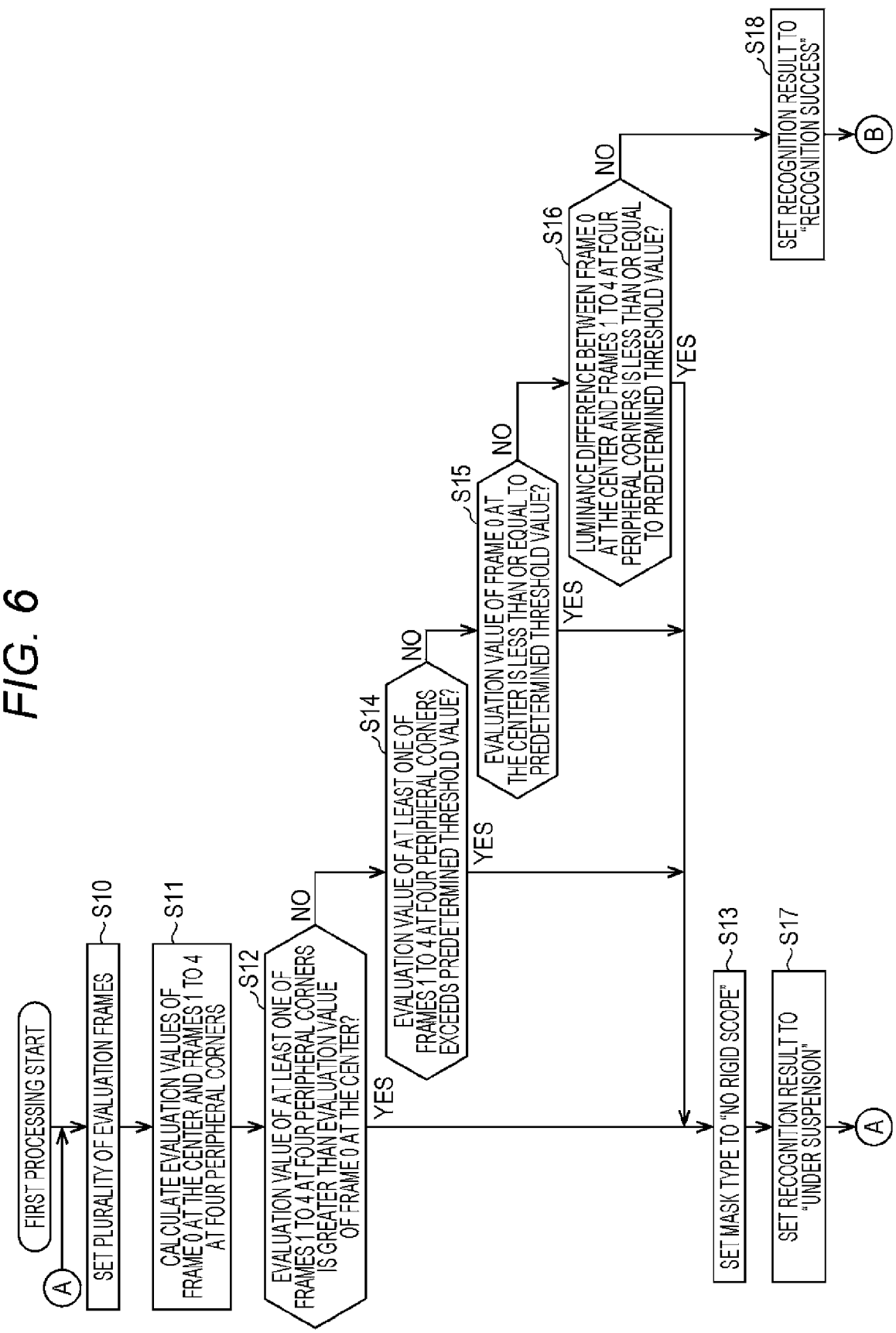
FIG. 6 is a flowchart explaining a flow of first processing.

Returning to the description of FIG. 6, in step S11, the evaluation value calculation unit 172 calculates the evaluation values corresponding to the frame 0 at the center and the frames 1 to 4 at the four peripheral corners illustrated in FIG. 7. As the evaluation value, for example, a feature value can be used obtained from the endoscopic image 200, such as a luminance value.

Note that, in the processing of step S11, for convenience of description, the evaluation values regarding the respective plurality of evaluation frames 210 are calculated at once, but the evaluation value regarding the target evaluation frame 210 may be calculated sequentially for each of determination processing steps (S12, S14, S15, S16) described later. The calculation method of the evaluation value is similar in the second processing to the fifth processing described later.

In step S12, the evaluation value determination unit 173 determines whether or not the evaluation value of at least one of the frames 1 to 4 at the four peripheral corners is larger than the evaluation value of the frame 0 at the center on the basis of a calculation result of the evaluation value of each frame.

In a case where it is determined in the determination processing of step S12 that the evaluation values of the frames 1 to 4 at the four peripheral corners are larger than the evaluation value of the frame 0 at the center, in other words, the central portion of the endoscopic image 200 is dark and the peripheral portion is bright, the processing proceeds to step S13. Then, in step S13, the evaluation result setting unit 174 sets the mask type to "no rigid scope".

Furthermore, in a case where it is determined in the determination processing of step S12 that the evaluation values of the frames 1 to 4 at the four peripheral corners are smaller than the evaluation value of the frame 0 at the center, the processing proceeds to step S14. In step S14, the evaluation value determination unit 173 determines whether or not the evaluation value of at least one of the frames 1 to 4 at the four peripheral corners exceeds a predetermined threshold value (first threshold value) on the basis of the calculation result of the evaluation value of the target frame.

In a case where it is determined in the determination processing of step S14 that the evaluation values of the frames 1 to 4 at the four peripheral corners exceed the predetermined threshold value, in other words, the entire image is bright, the processing proceeds to step S13, and "no rigid scope" is set as the mask type.

Furthermore, in a case where it is determined in the determination processing of step S14 that the evaluation values of the frames 1 to 4 at the four peripheral corners are less than or equal to the predetermined threshold value, the processing proceeds to step S15. In step S15, the evaluation value determination unit 173 determines whether or not the evaluation value of the frame 0 at the center is less than or equal to a predetermined threshold value (second threshold value) on the basis of the calculation result of the evaluation value of the target frame.

In a case where it is determined in the determination processing of step S15 that the evaluation value of the frame 0 at the center is less than or equal to the threshold value, in other words, the endoscopic image 200 reflects a black image overall, the processing proceeds to step S13, and "no rigid scope" is set as the mask type.

Furthermore, in a case where it is determined in the determination processing of step S15 that the evaluation value of the frame 0 at the center exceeds the predetermined threshold value, the processing proceeds to step S16. In step S16, the evaluation value determination unit 173 determines whether or not luminance differences between the frame 0 at the center and the frames 1 to 4 at the four peripheral corners are less than or equal to a predetermined threshold value (third threshold value) on the basis of the calculation result of the evaluation value of the target frame.

In a case where it is determined in the determination processing of step S16 that the luminance differences are less than or equal to the predetermined threshold value, the processing proceeds to step S13, and "no rigid scope" is set as the mask type.

Note that, in a case where it is determined as affirmative ("Yes") in the determination processing of steps S12, S14, S15, and S16, "no rigid scope" is set as the mask type (S13), and the processing proceeds to step S17. Then, in step S17, the evaluation result setting unit 174 sets the recognition result to "under suspension". Thereafter, the processing returns to step S10, and the above-described first processing is repeated.

Furthermore, in a case where it is determined in the determination processing of step S16 that the luminance differences exceed the predetermined threshold value, the processing proceeds to step S18. In step S18, the evaluation result setting unit 174 sets the recognition result to "recognition success". Thereafter, in the CCU 51, the second processing is executed following the first processing. Note that, details of the second processing will be described later with reference to FIG. 8 and the like.

The flow of the first processing has been described above. In the first processing, as illustrated in FIG. 7, the frame 0 at the center and the frames 1 to 4 at the four peripheral corners are set as the evaluation frames 210 for the endoscopic image 200, and it is determined whether or not the endoscopic image 200 includes the mask area on the basis of the relationship (correlation) between the evaluation values regarding the respective evaluation frames 210. Then, while the first processing is repeated in a case where the mask area is not included, the second processing is executed in a case where the mask area is included.

(Flow of Second Processing)

Next, a flow of the second processing executed by the CCU 51 will be described with reference to a flowchart of FIG. 8.

Figure 9:
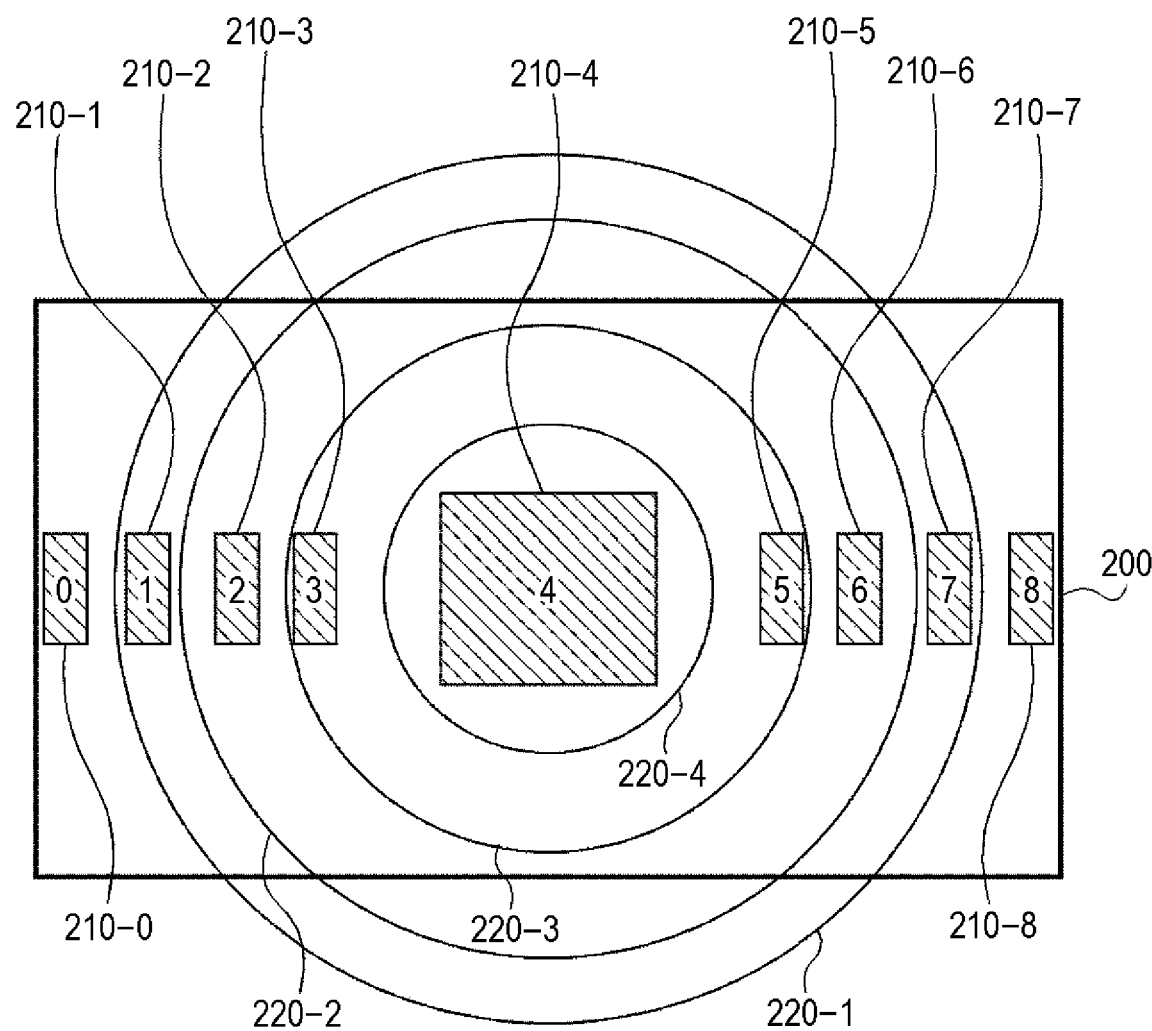
FIG. 9 is a diagram illustrating an example of a plurality of evaluation frames set in the second processing.

In step S30, the evaluation frame setting unit 171 sets a plurality of evaluation frames for the image corresponding to the image signal from the camera head 102. In the setting of the evaluation frames, as illustrated in FIG. 9, evaluation frames 210 are respectively provided at the central portion, and portions in the horizontal direction (X direction) of the endoscopic image 200.

Specifically, in the endoscopic image 200, a rectangular evaluation frame 210-4 (hereinafter referred to as an evaluation frame 4) is provided at the central portion including the approximate center of gravity.

Furthermore, rectangular evaluation frames 210-0 to 210-3 (hereinafter also simply referred to as evaluation frames 0, 1, 2, and 3) are provided at predetermined intervals on the left side in the horizontal direction, and rectangular evaluation frames 210-5 to 210-8 (hereinafter also simply referred to as evaluation frames 5, 6, 7, and 8) are provided at the predetermined intervals on the right side in the horizontal direction, to be substantially symmetric about (the approximate center of gravity included in) the central portion of the endoscopic image 200.

However, the sizes of the rectangles of the evaluation frames 210-0 to 210-3 and the evaluation frames 210-5 to 210-8 discretely arranged at the predetermined intervals on the left and right of the central portion are smaller than the size of the rectangle of the evaluation frame 210-4. Note that, in the present disclosure, "discretely" means that the plurality of evaluation frames 210 is not arranged continuously.

In FIG. 9, to determine which (mask type of the) mask edge 220 corresponds to the diameter of the scope 101 used, among the mask edges 220-1 to 220-4, the evaluation frames 0 to 8 are discretely provided at the predetermined intervals in the horizontal direction in the endoscopic image 200.

Specifically, for example, since the positions where the mask edge 220-1 is detected are known on the design, the evaluation frames 0 and 1, and the evaluation frames 7 and 8 are provided so that the detection positions of the mask edge 220-1 are between the evaluation frames 210.

Similarly, the evaluation frames are provided so that the detection positions of the mask edge 220-2 are between the evaluation frames 1 and 2 and between the evaluation frames 6 and 7, the detection positions of the mask edge 220-3 are between the evaluation frames 2 and 3 and between the evaluation frames 5 and 6, and the detection positions of the mask edge 220-4 are between the evaluation frames 3 and 4 and between the evaluation frames 4 and 5.

Figure 8:
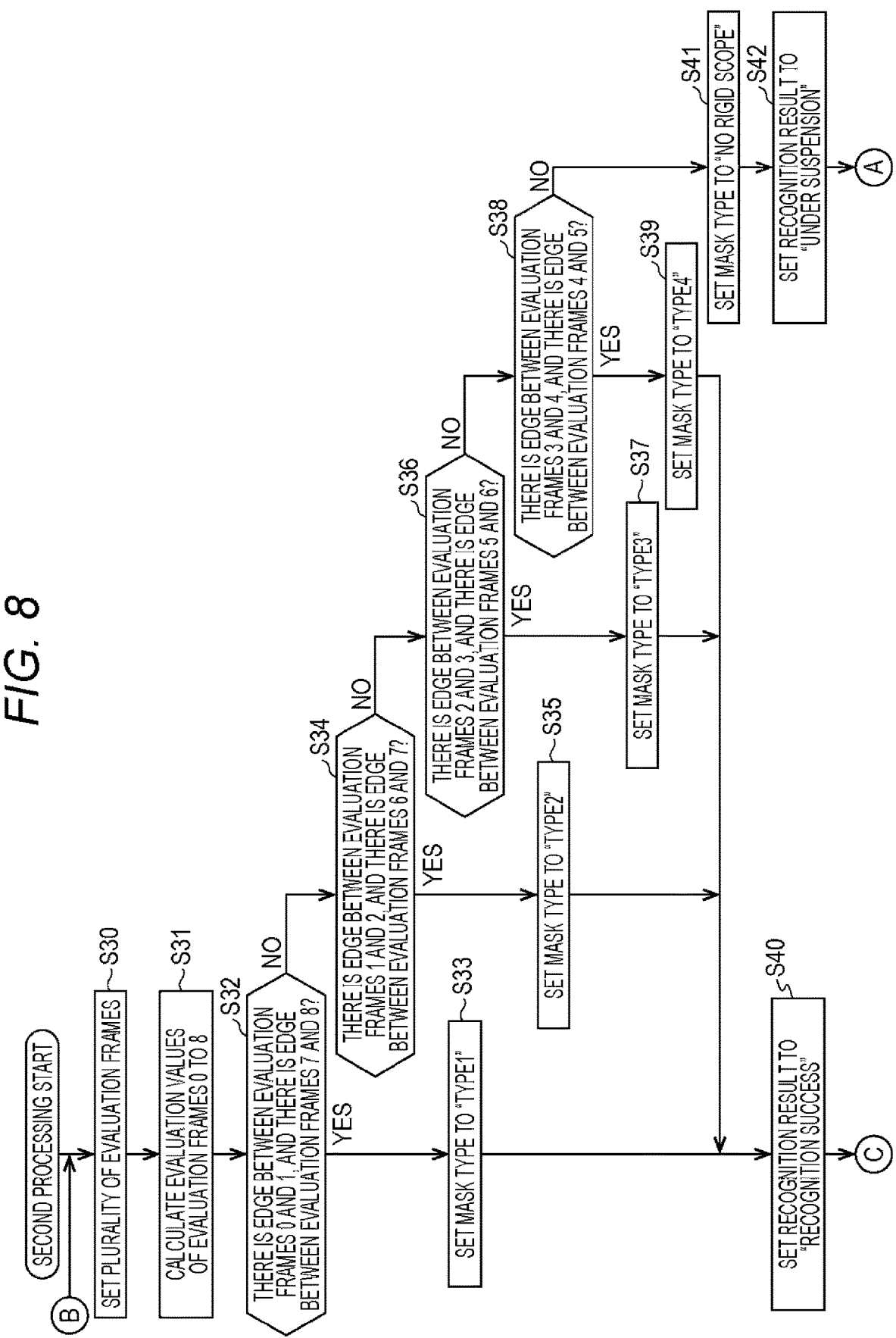
FIG. 8 is a flowchart explaining a flow of second processing.

Returning to the description of FIG. 8, in step S31, the evaluation value calculation unit 172 calculates evaluation values corresponding to the evaluation frames 0 to 8 illustrated in FIG. 9. As the evaluation value, for example, a feature value can be used obtained from the endoscopic image 200, such as a luminance value.

In step S32, the evaluation value determination unit 173 determines whether or not there is an edge between the evaluation frames 0 and 1, and there is an edge between the evaluation frames 7 and 8 on the basis of the calculation results of the evaluation values of the evaluation frames 0 and 1, and the evaluation frames 7 and 8.

Here, for example, a difference between a luminance value obtained from the evaluation frame 0 and a luminance value obtained from the evaluation frame 1, and a difference between a luminance value obtained from the evaluation frame 7 and a luminance value obtained from the evaluation frame 8 each are compared with a predetermined threshold value (fourth threshold value), and it is determined whether or not those luminance differences exceed the predetermined threshold value, whereby it can be determined whether or not there is an edge (mask edge 220-1) between those evaluation frames 210.

In a case where it is determined as affirmative ("Yes") in the determination processing of step S32, the processing proceeds to step S33. In step S33, the evaluation result setting unit 174 sets the mask type to "TYPE1".

Furthermore, in a case where it is determined as negative ("No") in the determination processing of step S32, the processing proceeds to step S34. In step S34, the evaluation value determination unit 173 determines whether or not there is an edge between the evaluation frames 1 and 2, and there is an edge between the evaluation frames 6 and 7 on the basis of the calculation results of the evaluation values of the evaluation frames 1 and 2, and the evaluation frames 6 and 7.

In a case where it is determined as affirmative in the determination processing of step S34, the processing proceeds to step S35. In step S35, the evaluation result setting unit 174 sets the mask type to "TYPE2".

Furthermore, in a case where it is determined as negative in the determination processing of step S34, the processing proceeds to step S36. In step S36, the evaluation value determination unit 173 determines whether or not there is an edge between the evaluation frames 2 and 3, and there is an edge between the evaluation frames 5 and 6 on the basis of the calculation results of the evaluation values of the evaluation frames 2 and 3, and the evaluation frames 5 and 6.

In a case where it is determined as affirmative in the determination processing of step S36, the processing proceeds to step S37. In step S37, the evaluation result setting unit 174 sets the mask type to "TYPE3".

Furthermore, in a case where it is determined as negative in the determination processing of step S36, the processing proceeds to step S38. In step S38, the evaluation value determination unit 173 determines whether or not there is an edge between the evaluation frames 3 and 4, and there is an edge between the evaluation frames 4 and 5 on the basis of the calculation results of the evaluation values of the evaluation frames 3 and 4, and the evaluation frames 4 and 5.

In a case where it is determined as affirmative in the determination processing of step S38, the processing proceeds to step S39. In step S39, the evaluation result setting unit 174 sets the mask type to "TYPE4".

Note that, in a case where it is determined as affirmative in the determination processing of steps S32, S34, S36, and S38, "TYPE1", "TYPE2", "TYPE3", and "TYPE4" are respectively set as mask types (S33, S35, S37, and S39), and the processing proceeds to step S40.

Then, in step S40, the evaluation result setting unit 174 sets the recognition result to "recognition success". Thereafter, in the CCU 51, the third processing is executed following the second processing. Note that, details of the third processing will be described later with reference to FIG. 10 and the like.

Furthermore, in a case where it is determined as negative in the determination processing of step S38, the processing proceeds to step S41. Then, the evaluation result setting unit 174 sets the mask type to "no rigid scope" (S41), and sets the recognition result to "under suspension" (S42). Thereafter, the processing returns to step S10 of FIG. 6, and the first processing described above is executed.

The flow of the second processing has been described above. In the second processing, as illustrated in FIG. 9, the evaluation frames 210-0 to 210-8 are discretely arranged at predetermined intervals in the horizontal direction for the endoscopic image 200, and a mask type depending on the position of the edge is set on the basis of the relationship (correlation) between the evaluation values regarding the respective evaluation frames 210. Then, while the first processing is repeated in a case where an edge corresponding to the evaluation frame 210 is not detected, the third processing is executed in a case where the edge corresponding to the evaluation frame 210 is detected.

(Flow of Third Processing)

Next, a flow of the third processing executed by the CCU 51 will be described with reference to a flowchart of FIG. 10.

In step S50, the evaluation result setting unit 174 determines whether or not the mask type is set to "TYPE3" or "TYPE4" in the second processing. In other words, in this example, since the detection positions in the vertical direction of the mask edges 220-1 and 220-2 that are "TYPE1" and "TYPE2" are positioned outside the endoscopic image 200, the processing regarding the mask edges 220-1 and 220-2 is excluded.

In a case where it is determined as affirmative in the determination processing of step S50, the processing proceeds to step S51. In step S51, the evaluation frame setting unit 171 sets a plurality of evaluation frames for the image corresponding to the image signal from the camera head 102.

Figure 11:
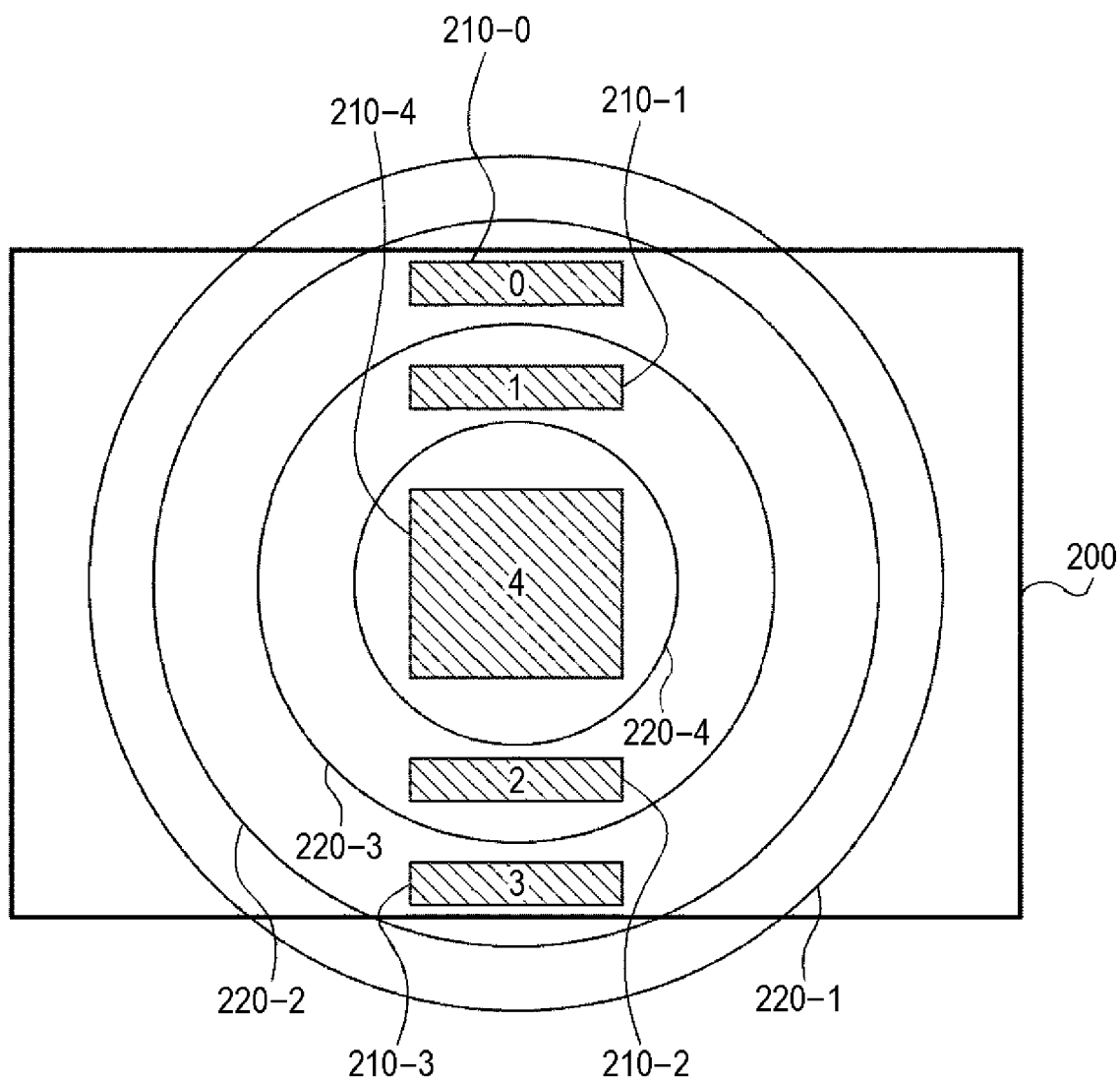
FIG. 11 is a diagram illustrating an example of a plurality of evaluation frames set in the third processing.

In the setting of the evaluation frames, as illustrated in FIG. 11, evaluation frames 210 are respectively provided at the central portion, and portions in the vertical direction (Y direction) of the endoscopic image 200. Specifically, in the endoscopic image 200, a rectangular evaluation frame 210-4 (hereinafter referred to as an evaluation frame 4) is provided at the central portion including the approximate center of gravity.

Furthermore, rectangular evaluation frames 210-0 and 210-1 (hereinafter also simply referred to as evaluation frames 0 and 1) are provided at a predetermined interval on the upper side in the vertical direction, and rectangular evaluation frames 210-2 and 210-3 (hereinafter also simply referred to as evaluation frames 2 and 3) are provided at the predetermined interval on the lower side in the vertical direction, to be substantially symmetric about (the approximate center of gravity included in) the central portion of the endoscopic image 200.

However, the sizes of the rectangles of the evaluation frames 210-0 and 210-1 and the evaluation frames 210-2 and 210-3 discretely arranged at the predetermined interval on the upper side and lower side of the central portion are smaller than the size of the rectangle of the evaluation frame 210-4.

In FIG. 11, to determine which (mask type of the) mask edge 220 corresponds to the diameter of the scope 101 used, among the mask edges 220-3 and 220-4, the evaluation frames 210-0 to 210-3 are provided discretely at the predetermined interval in the vertical direction in the endoscopic image 200.

Specifically, the evaluation frames are provided so that the detection positions of the mask edge 220-3 are between the evaluation frames 0 and 1 and between the evaluation frames 2 and 3, and the detection positions of the mask edge 220-4 are between the evaluation frames 1 and 4 and between the evaluation frames 2 and 4.

Figure 10:
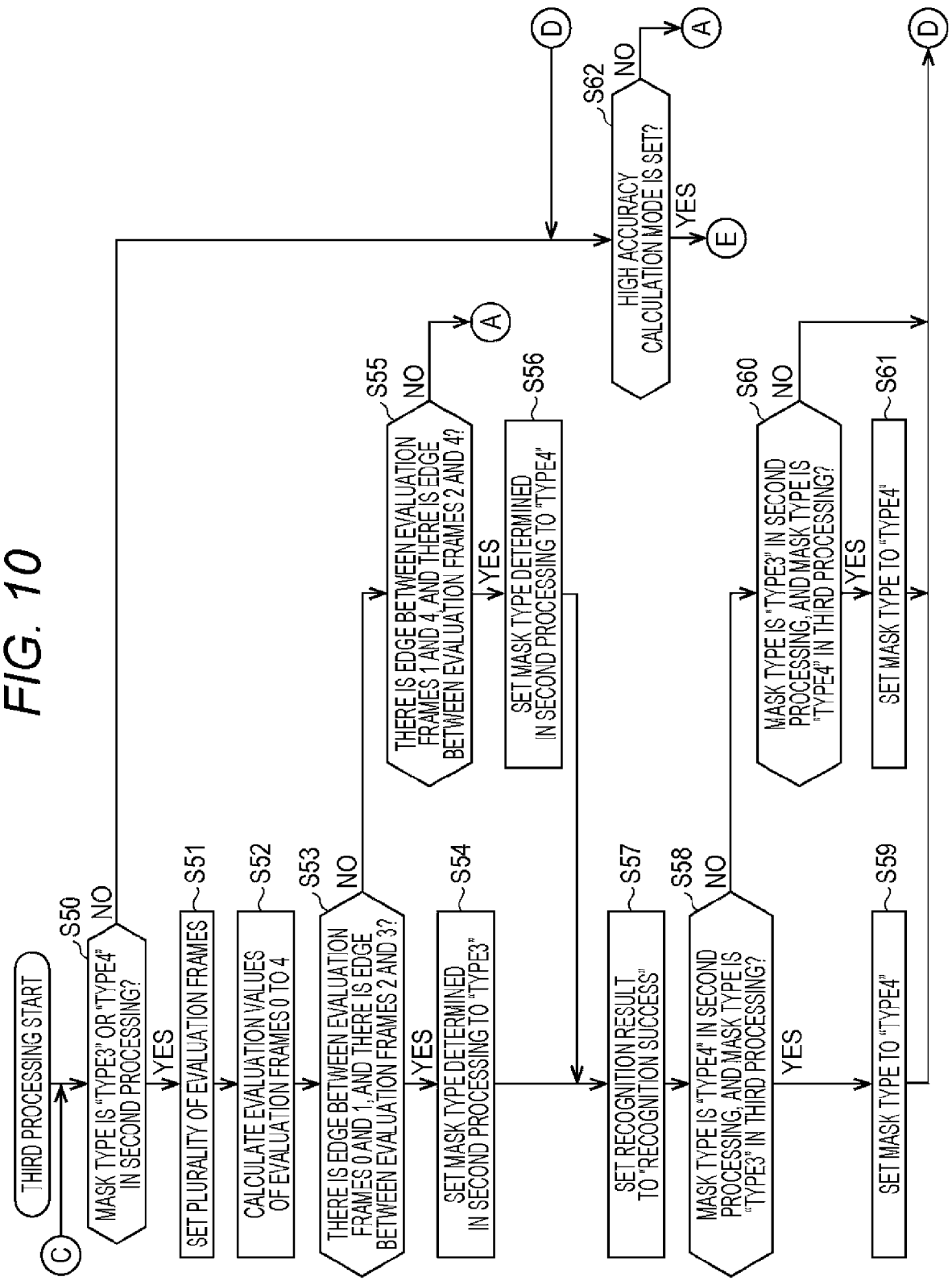
FIG. 10 is a flowchart explaining a flow of third processing.

Returning to the description of FIG. 10, in step S52, the evaluation value calculation unit 172 calculates evaluation values corresponding to the evaluation frames 0 to 4 illustrated in FIG. 11. As the evaluation value, for example, a feature value can be used obtained from the endoscopic image 200, such as a luminance value.

In step S53, the evaluation value determination unit 173 determines whether or not there is an edge between the evaluation frames 0 and 1, and there is an edge between the evaluation frames 2 and 3 on the basis of the calculation results of the evaluation values of the evaluation frames 0 and 1, and the evaluation frames 2 and 3.

Here, for example, a difference between a luminance value obtained from the evaluation frame 0 and a luminance value obtained from the evaluation frame 1, and a difference between a luminance value obtained from the evaluation frame 2 and a luminance value obtained from the evaluation frame 3 each are compared with a predetermined threshold value (fifth threshold value), and it is determined whether or not those luminance differences exceed the predetermined threshold value, whereby it can be determined whether or not there is an edge (mask edge 220-3) between those evaluation frames 210.

In a case where it is determined as affirmative in the determination processing of step S53, the processing proceeds to step S54. In step S54, the evaluation result setting unit 174 sets the mask type determined in the second processing to "TYPE3".

Furthermore, in a case where it is determined as negative in the determination processing of step S53, the processing proceeds to step S55. In step S55, the evaluation value determination unit 173 determines whether or not there is an edge between the evaluation frames 1 and 4, and there is an edge between the evaluation frames 2 and 4 on the basis of the calculation results of the evaluation values of the evaluation frames 1 and 4, and the evaluation frames 2 and 4.

In a case where it is determined as affirmative in the determination processing of step S55, the processing proceeds to step S56. In step S56, the evaluation result setting unit 174 sets the mask type determined in the second processing to "TYPE4".

When the processing of step S54 or S56 ends, the processing proceeds to step S57. Then, in step S57, the evaluation result setting unit 174 sets the recognition result to "recognition success".

In step S58, the evaluation result setting unit 174 determines whether or not the mask type determined in the second processing is set to "TYPE4" and the mask type determined in the third processing is set to "TYPE3".

In a case where it is determined as affirmative in the determination processing of step S58, the processing proceeds to step S59. In step S59, the evaluation result setting unit 174 sets the mask type to "TYPE4". In other words, in this case, it is assumed that, for example, the mask diameter in the vertical direction is detected larger due to light leakage, the mask diameter detected in the horizontal direction in the second processing is adopted. As described above, a narrower mask diameter is selected and determined, whereby the black area can be prevented from being included more reliably when subsequent processing is performed, for example.

Furthermore, in a case where it is determined as negative in the determination processing of step S58, the processing proceeds to step S60. In step S60, the evaluation value determination unit 173 determines whether or not the mask type determined in the second processing is set to "TYPE3" and the mask type determined in the third processing is set to "TYPE4".

In a case where it is determined as affirmative in the determination processing of step S60, the processing proceeds to step S61. In step S61, the evaluation result setting unit 174 sets the mask type to "TYPE4". In other words, in this case, it is assumed that, for example, the mask diameter in the horizontal direction is detected larger due to light leakage, the mask diameter detected in the vertical direction in the third processing is adopted so that the black area is prevented from being included more reliably.

In a case where the processing of step S59 or S61 ends, or it is determined as negative in the determination processing of step S60, the processing proceeds to step S62. Moreover, also in a case where it is determined as negative in the determination processing of step S50 described above, the processing proceeds to step S62.

In step S62, it is determined whether or not the operation mode is set to a high accuracy calculation mode that is a mode for calculating a mask diameter size more accurately than a normal mode.

In a case where it is determined as affirmative in the determination processing of step S62, in the CCU 51, the fourth processing is executed following the third processing. Note that, details of the fourth processing will be described later with reference to FIG. 12 and the like.

Furthermore, in a case where it is determined as negative in the determination processing of step S62, the processing returns to step S10 of FIG. 6, and the first processing described above is executed. Note that, also in a case where it is determined as negative in the determination processing of step S55, the first processing described above is executed similarly.

The flow of the third processing has been described above. In the third processing, as illustrated in FIG. 11, the evaluation frames 210-0 to 210-4 are discretely set at predetermined intervals in the vertical direction for the endoscopic image 200, and a mask type depending on the position of the edge is set (reset) on the basis of the relationship (correlation) between the evaluation values regarding the respective evaluation frames 210. Then, while the processing returns to the first processing in a case where the normal mode is set as the operation mode, the fourth processing is executed in a case where the high accuracy calculation mode is set.

Here, in a case where operation is performed in the normal mode, one of "TYPE1" to "TYPE4" is set on the basis of relevance of the evaluation values corresponding to the respective plurality of evaluation frames 210 by the second processing and the third processing, and the type estimation unit 175 can estimate the diameter of the scope 101 by obtaining the mask diameter size on the basis of the mask type set. For example, in a case where the mask type is set to "TYPE4" by the second processing and the third processing, the mask edge 220-4 is detected, so that the mask diameter can be obtained.

Furthermore, here, the center position of the mask can also be obtained in the horizontal and vertical directions. For example, in a case where the mask edge 220-4 is detected, as illustrated in FIG. 11, coordinates (x, y) of the center position of the mask can be calculated by using coordinates of vertices of the rectangles of the evaluation frames 210-1 and 210-2.

Specifically, for example, in FIG. 11, with a position of the upper left vertex of the endoscopic image 200 as the origin (0, 0), when coordinates of the lower right vertex of the rectangle of the evaluation frame 210-1 are coordinates (x0, y0) and coordinates of the upper left vertex of the rectangle of the evaluation frame 210-2 are coordinates (x1, y1), the center position (x, y) of the mask in the horizontal and vertical directions is obtained by the following equations (1) and (2).

$$x=(x0-x1)/2+x1 \quad (1)$$

$$y=(y1-y0)/2+y0 \quad (2)$$

As described above, in a case where the operation is performed in the normal mode, although the accuracy is lower than in a case where the operation is performed in the high accuracy calculation mode, the diameter and center position of the mask can be calculated, the diameter and center position of the scope 101 can be estimated, and the type of the scope 101 can be determined, with a smaller amount of calculation.

Furthermore, in the second processing and the third processing, since the plurality of evaluation frames 210 is discretely provided at the predetermined interval for the endoscopic image 200 and the evaluation frames 210 are separated from each other at the predetermined interval, an error can be reduced that occurs in attachment of the scope 101, for example.

Note that, in the above description, a case has been described where evaluation is performed by setting the evaluation frames 210 in both directions of the horizontal and vertical directions so that the plurality of evaluation frames 210 is point-symmetrical with respect to the approximate center of gravity of the endoscopic image 200 by executing the second processing and the third processing; however, the evaluation may be performed by setting the evaluation frames 210 only in one of the horizontal and vertical directions by executing the second processing or the third processing. However, as described above, when the evaluation frames 210 are set in both directions of the horizontal and vertical directions by executing the second processing and the third processing, it is possible to set the mask type assuming that, for example, there is light leakage or the like, so that the mask diameter and the center position can be obtained more accurately.

Furthermore, in the second processing and the third processing, a case has been described where the plurality of evaluation frames 210 is discretely arranged at the predetermined interval, i.e., adjacent frames have an interval therebetween; however, part of the evaluation frames 210 may be continuously arranged. Furthermore, the number of the plurality of evaluation frames 210 discretely arranged is arbitrary, and for example, a larger number of evaluation frames 210 may be provided for the detection position of the mask edge 220. Moreover, the shape of each of the evaluation frames 210 discretely arranged is not limited to a rectangle, and may be another shape, and it is not necessary that all the evaluation frames 210 have the same shape. The intervals at which the plurality of evaluation frames 210 is arranged do not have to be constant intervals.

Moreover, in the second processing and the third processing, an example has been described in which an edge (mask edge 220) is detected by using a luminance value as an evaluation value and comparing a luminance difference with a predetermined threshold value; however, the edge may be detected by using, as the evaluation value, a quantitative value (for example, a feature value such as an edge amount or a black area amount) representing an edge, a black area, or the like included in the frame 210.

(Flow of Fourth Processing)

Next, a flow of the fourth processing executed by the CCU 51 will be described with reference to flowcharts of FIGS. 12 and 13. However, in the fourth processing, in particular, a case will be described where "TYPE3" is set as the mask type in the second processing and the third processing described above.

Figure 14:
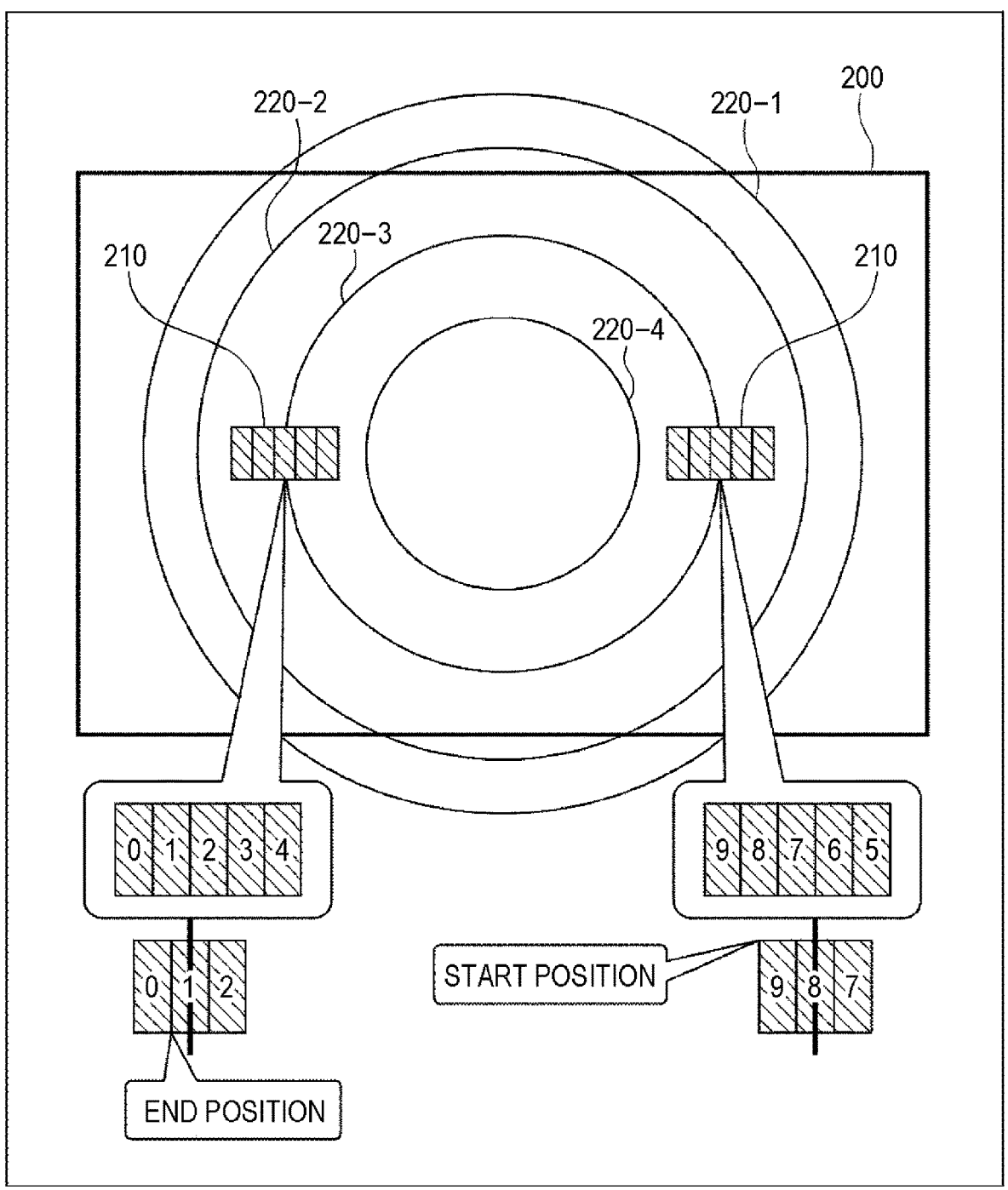
FIG. 14 is a diagram illustrating an example of a plurality of evaluation frames set in the fourth processing.

In step S70, the evaluation frame setting unit 171 sets a plurality of evaluation frames for the image corresponding to the image signal from the camera head 102. In the setting of the evaluation frames, since "TYPE3" is set as the mask type, as illustrated in FIG. 14, a plurality of evaluation frames 210 is provided depending on the detection position of the mask edge 220-3. In contrast to the plurality of evaluation frames in FIGS. 7, 9, and 11, which are spatially separated and discrete, the plurality of evaluation frames in FIG. 14 are spatially separated and continuous, i.e., adjacent frames abut with no interval therebetween, allowing for higher accuracy detection of the edge along the horizontal direction.

Specifically, evaluation frames 210-0 to 210-4 (hereinafter also simply referred to as evaluation frames 0, 1, 2, 3, and 4) corresponding to the detection position of the mask edge 220-3 are provided continuously on the left side in the horizontal direction, and evaluation frames 210-5 to 210-9 (hereinafter also simply referred to as evaluation frames 5, 6, 7, 8, and 9) corresponding to the detection position of the mask edge 220-3 are provided continuously on the right side in the horizontal direction, to be substantially symmetric about the approximate center of gravity of the endoscopic image 200 (left-right symmetry with the Y-axis as the symmetry axis).

However, the rectangles of the evaluation frames 210-0 to 210-4 and the rectangles of the evaluation frames 210-5 to 210-9 continuously arranged in left-right symmetry have substantially the same shape and substantially the same size.

Furthermore, in each evaluation frame 210, a start position and an end position are provided in the horizontal direction (X direction). The start position indicates the position of the left end in the X direction of each evaluation frame 210, and the end position indicates the position of the right end in the X direction of each evaluation frame 210.

Figure 12:
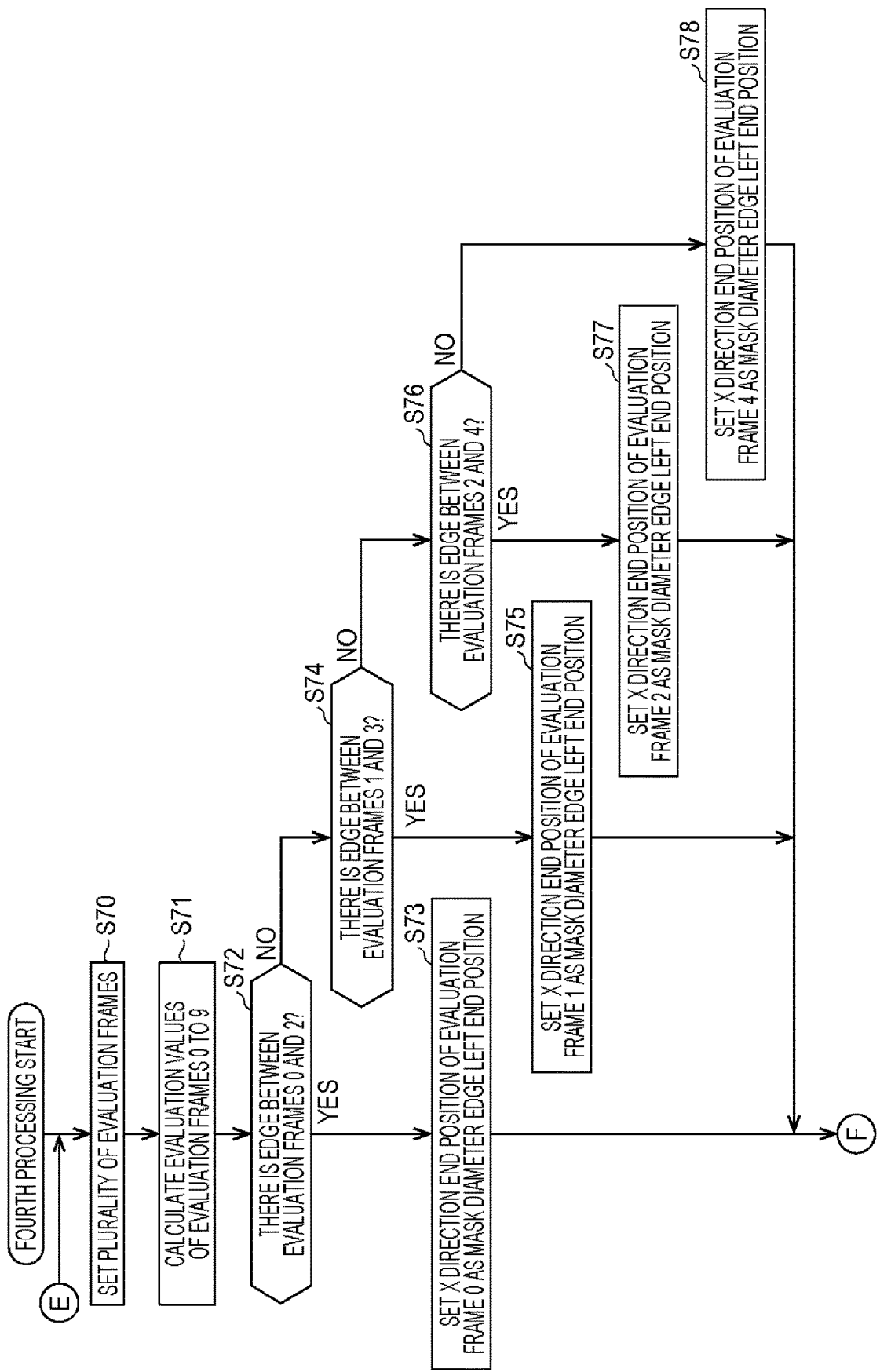
FIG. 12 is a flowchart explaining a flow of fourth processing.

Returning to the description of FIG. 12, in step S71, the evaluation value calculation unit 172 calculates evaluation values corresponding to the evaluation frames 0 to 9 illustrated in FIG. 14. As the evaluation value, for example, a feature value can be used obtained from the endoscopic image 200, such as a luminance value.

In step S72, the evaluation value determination unit 173 determines whether or not there is an edge between the evaluation frames 0 and 2 on the basis of the calculation results of the evaluation values of the evaluation frames 0 and 2.

Here, for example, a difference between a luminance value obtained from the evaluation frame 0 and a luminance value obtained from the evaluation frame 2 is compared with a predetermined threshold value (sixth threshold value), and it is determined whether or not the luminance difference exceeds the predetermined threshold value, whereby it can be determined whether or not there is an edge (in this example, the mask edge 220-3) between the evaluation frames 0 and 2.

In a case where it is determined as affirmative in the determination processing of step S72, the processing proceeds to step S73. In step S73, the evaluation result setting unit 174 sets the X direction end position of the evaluation frame 0 as the mask diameter edge left end position.

Furthermore, in a case where it is determined as negative in the determination processing of step S72, the processing proceeds to step S74. In step S74, the evaluation value determination unit 173 determines whether or not there is an edge between the evaluation frames 1 and 3 on the basis of the calculation results of the evaluation values of the evaluation frames 1 and 3.

In a case where it is determined as affirmative in the determination processing of step S74, the processing proceeds to step S75. In step S75, the evaluation result setting unit 174 sets the X direction end position of the evaluation frame 1 as the mask diameter edge left end position.

Furthermore, in a case where it is determined as negative in the determination processing of step S74, the processing proceeds to step S76. In step S76, the evaluation value determination unit 173 determines whether or not there is an edge between the evaluation frames 2 and 4 on the basis of the calculation results of the evaluation values of the evaluation frames 2 and 4.

In a case where it is determined as affirmative in the determination processing of step S76, the processing proceeds to step S77. In step S77, the evaluation result setting unit 174 sets the X direction end position of the evaluation frame 2 as the mask diameter edge left end position.

Furthermore, in a case where it is determined as negative in the determination processing of step S76, the processing proceeds to step S78. In step S78, the evaluation result setting unit 174 sets the X direction end position of the evaluation frame 4 as the mask diameter edge left end position.

Figure 13:
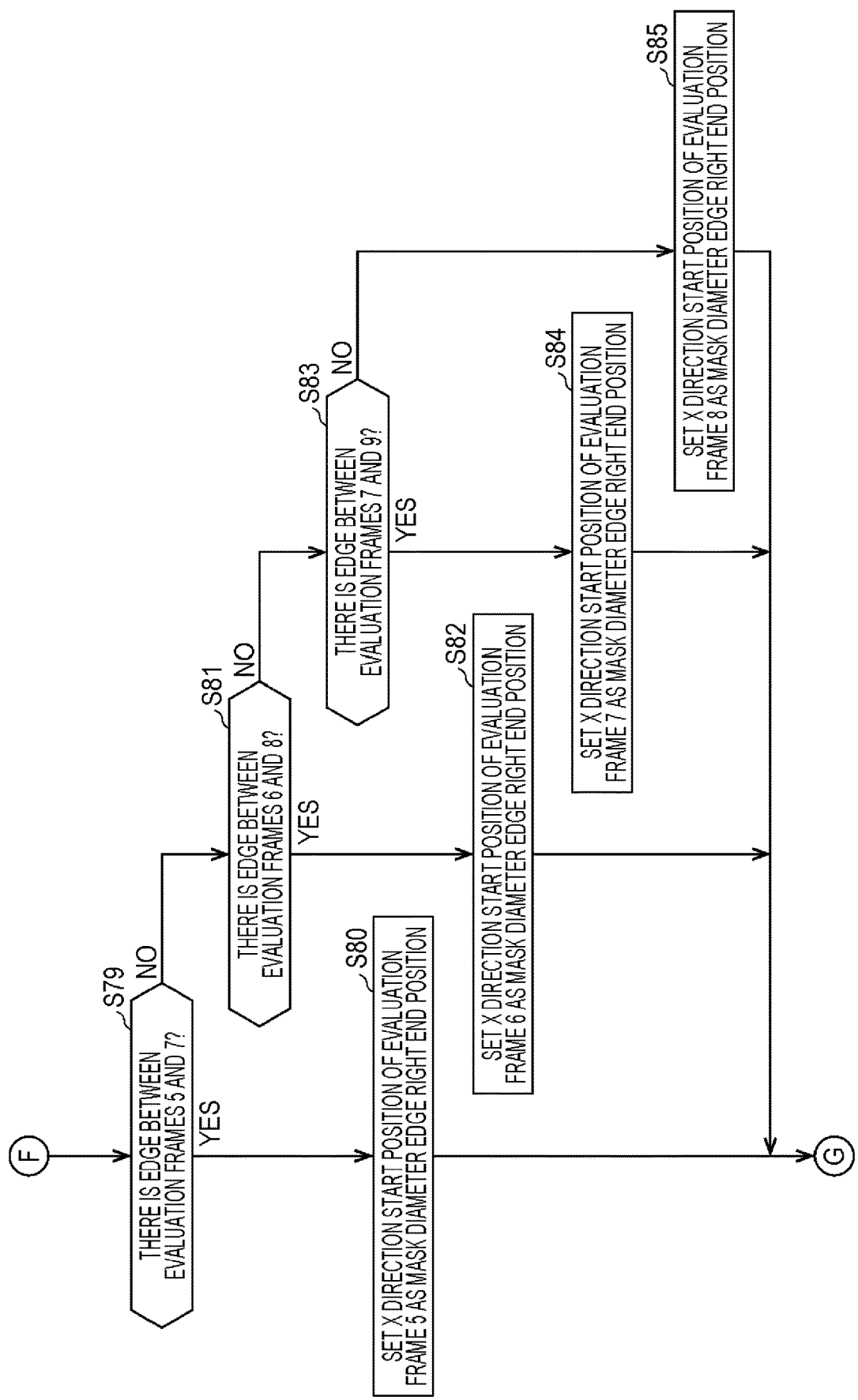
FIG. 13 is a flowchart explaining a flow of fourth processing.

When the mask diameter edge left end position is set in the processing of step S73, S75, S77, or S78, the processing proceeds to step S79 of FIG. 13.

In step S79, the evaluation value determination unit 173 determines whether or not there is an edge between the evaluation frames 5 and 7 on the basis of the calculation results of the evaluation values of the evaluation frames 5 and 7.

In a case where it is determined as affirmative in the determination processing of step S79, the processing proceeds to step S80. In step S80, the evaluation result setting unit 174 sets the X direction start position of the evaluation frame 5 as the mask diameter edge right end position.

Furthermore, in a case where it is determined as negative in the determination processing of step S79, the processing proceeds to step S81. In step S81, the evaluation value determination unit 173 determines whether or not there is an edge between the evaluation frames 6 and 8 on the basis of the calculation results of the evaluation values of the evaluation frames 6 and 8.

In a case where it is determined as affirmative in the determination processing of step S81, the processing proceeds to step S82. In step S82, the evaluation result setting unit 174 sets the X direction start position of the evaluation frame 6 as the mask diameter edge right end position.

Furthermore, in a case where it is determined as negative in the determination processing of step S81, the processing proceeds to step S83. In step S83, the evaluation value determination unit 173 determines whether or not there is an edge between the evaluation frames 7 and 9 on the basis of the calculation results of the evaluation values of the evaluation frames 7 and 9.

In a case where it is determined as affirmative in the determination processing of step S83, the processing proceeds to step S84. In step S84, the evaluation result setting unit 174 sets the X direction start position of the evaluation frame 7 as the mask diameter edge right end position.

Furthermore, in a case where it is determined as negative in the determination processing of step S83, the processing proceeds to step S85. In step S85, the evaluation result setting unit 174 sets the X direction start position of the evaluation frame 8 as the mask diameter edge right end position.

When the mask diameter edge right end position is set in the processing of step S80, S82, S84, or S85, in the CCU 51, the fifth processing is executed following the fourth processing. Note that, details of the fifth processing will be described later with reference to FIG. 15 and the like.

The flow of the fourth processing has been described above. In the fourth processing, processing for calculating a detailed mask edge in the horizontal direction (X direction) is performed depending on the evaluation results in the second processing and the third processing described above, and as illustrated in FIG. 14, the evaluation frames 210-0 to 210-4 and the evaluation frames 210-5 to 210-9 are continuously arranged in left-right symmetry in the horizontal direction for the endoscopic image 200, and the edge left end position and the edge right end position in the mask diameter are set on the basis of the relationship (correlation) between the evaluation values regarding the respective evaluation frames 210.

(Flow of Fifth Processing)

Next, a flow of the fifth processing executed by the CCU 51 will be described with reference to flowcharts of FIGS. 15 and 16. However, in the fifth processing, similarly to the fourth processing described above, a case will be described where "TYPE3" is set as the mask type in the second processing and the third processing described above.

In step S90, the evaluation result setting unit 174 determines whether or not the mask type is set to "TYPE3" or "TYPE4" in the second processing.

In a case where it is determined as affirmative in the determination processing of step S90, the processing proceeds to step S91. In step S91, the evaluation frame setting unit 171 sets a plurality of evaluation frames for the image corresponding to the image signal from the camera head 102.

Figure 17:
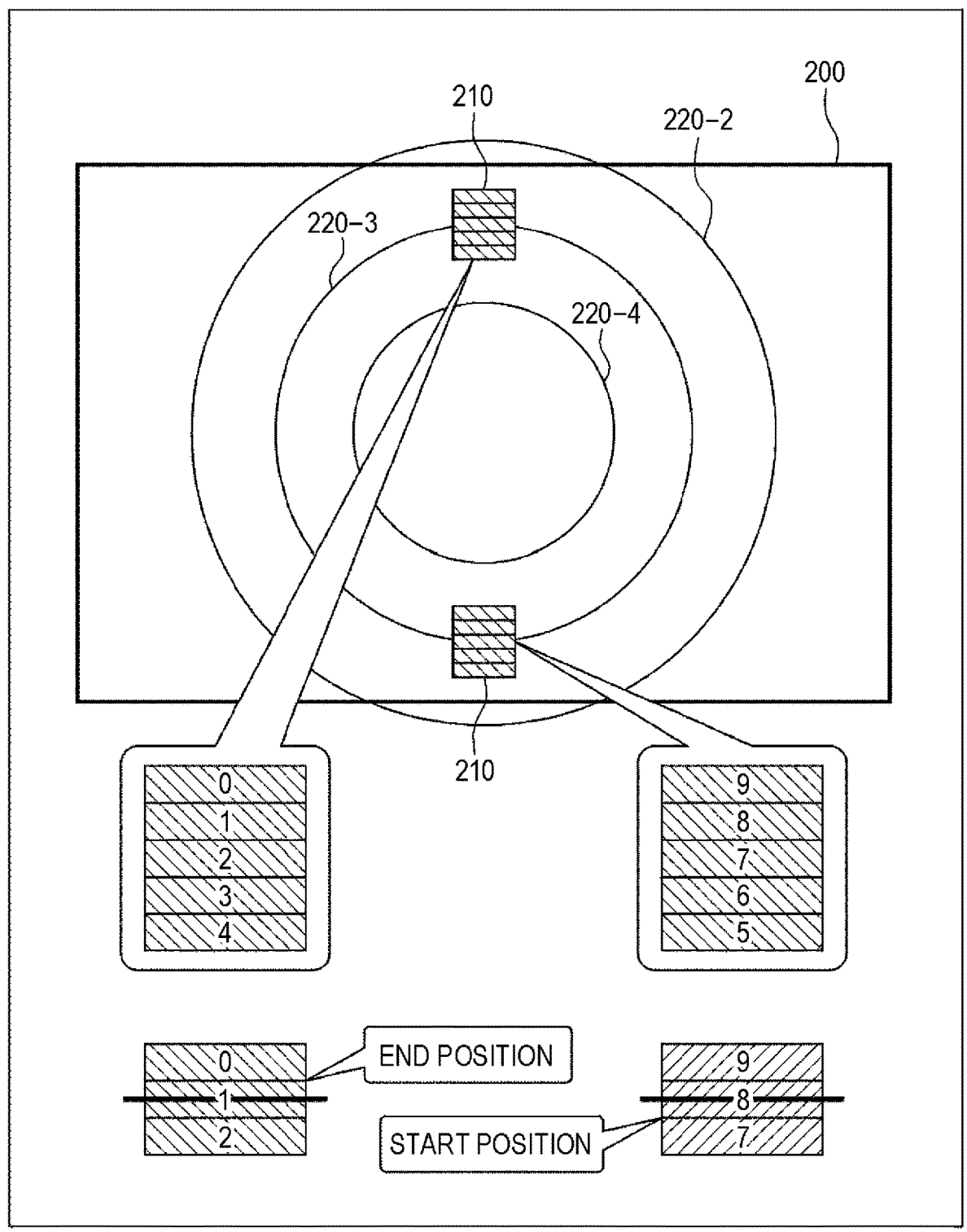
FIG. 17 is a diagram illustrating an example of a plurality of evaluation frames in the fifth processing.

In the setting of the evaluation frames, since "TYPE3" is set as the mask type, as illustrated in FIG. 17, a plurality of evaluation frames 210 is provided depending on the detection position of the mask edge 220-3. The plurality of evaluation frames in FIG. 17 are spatially separated and continuous, allowing for higher accuracy detection of the edge along the vertical direction.

Specifically, evaluation frames 210-0 to 210-4 (hereinafter also simply referred to as evaluation frames 0, 1, 2, 3, and 4) corresponding to the detection position of the mask edge 220-3 are provided continuously on the upper side in the vertical direction, and evaluation frames 210-5 to 210-9 (hereinafter also simply referred to as evaluation frames 5, 6, 7, 8, and 9) corresponding to the detection position of the mask edge 220-3 are provided continuously on the lower side in the vertical direction, to be substantially symmetric about the approximate center of gravity of the endoscopic image 200 (vertical symmetry with the X-axis as the symmetry axis).

However, the rectangles of the evaluation frames 210-0 to 210-4 and the rectangles of the evaluation frames 210-5 to 210-9 continuously arranged in vertical symmetry have substantially the same shape and substantially the same size.

Furthermore, in each evaluation frame 210, a start position and an end position are provided in the vertical direction (Y direction). The start position indicates the position of the upper end in the Y direction of each evaluation frame 210, and the end position indicates the position of the lower end in the Y direction of each evaluation frame 210.

Figure 15:
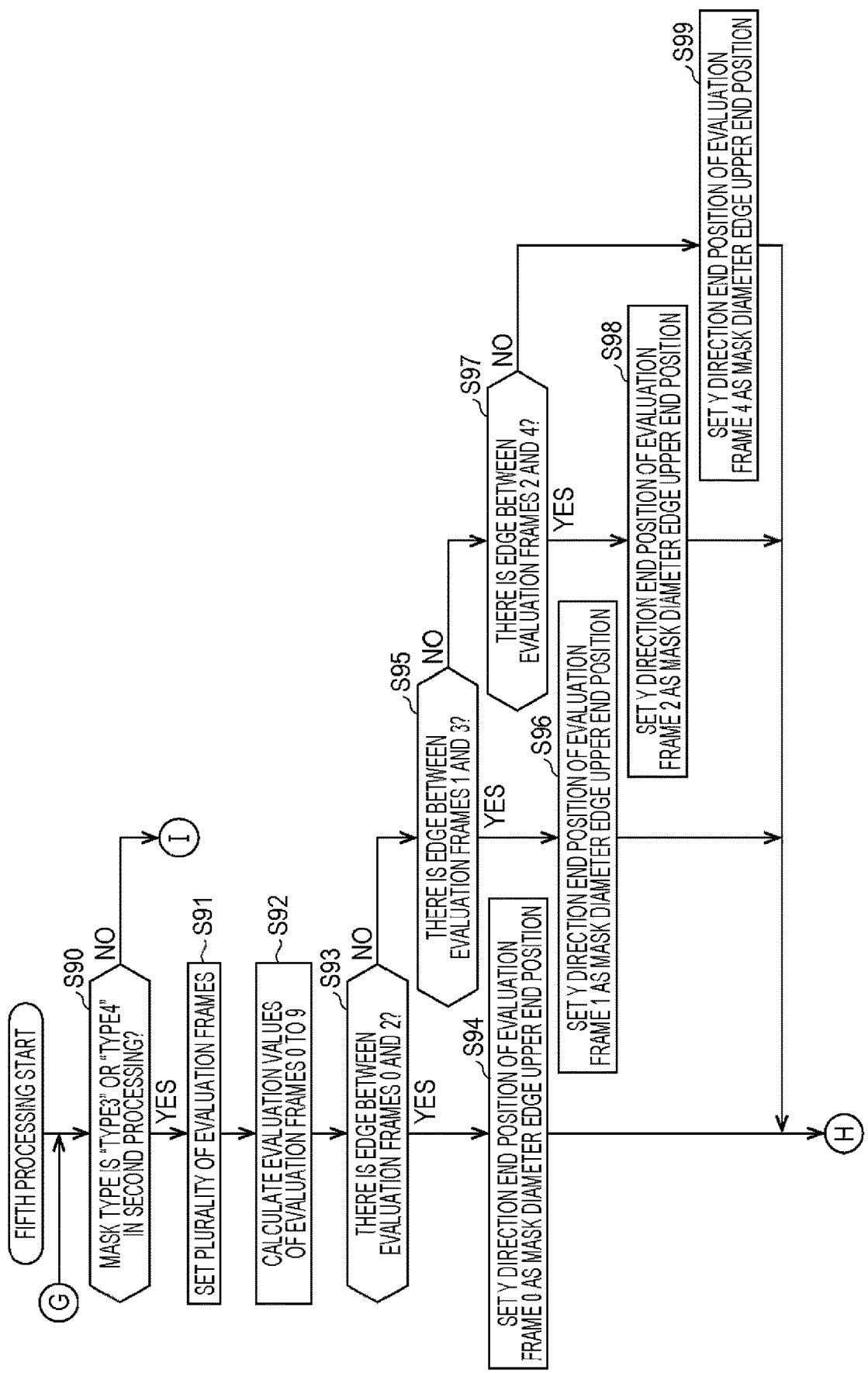
FIG. 15 is a flowchart explaining a flow of fifth processing.

Returning to the description of FIG. 15, in step S92, the evaluation value calculation unit 172 calculates evaluation values corresponding to the evaluation frames 0 to 9 illustrated in FIG. 17. As the evaluation value, for example, a feature value can be used obtained from the endoscopic image 200, such as a luminance value.

In step S93, the evaluation value determination unit 173 determines whether or not there is an edge between the evaluation frames 0 and 2 on the basis of the calculation results of the evaluation values of the evaluation frames 0 and 2.

Here, for example, a difference between a luminance value obtained from the evaluation frame 0 and a luminance value obtained from the evaluation frame 2 is compared with a predetermined threshold value (seventh threshold value), and it is determined whether or not the luminance difference exceeds the predetermined threshold value, whereby it can be determined whether or not there is an edge (in this example, the mask edge 220-3) between the evaluation frames 0 and 2.

In a case where it is determined as affirmative in the determination processing of step S93, the processing proceeds to step S94. In step S94, the evaluation result setting unit 174 sets the Y direction end position of the evaluation frame 0 as the mask diameter edge upper end position.

Furthermore, in a case where it is determined as negative in the determination processing of step S93, the processing proceeds to step S95. In step S95, the evaluation value determination unit 173 determines whether or not there is an edge between the evaluation frames 1 and 3 on the basis of the calculation results of the evaluation values of the evaluation frames 1 and 3.

In a case where it is determined as affirmative in the determination processing of step S95, the processing proceeds to step S96. In step S96, the evaluation result setting unit 174 sets the Y direction end position of the evaluation frame 1 as the mask diameter edge upper end position.

Furthermore, in a case where it is determined as negative in the determination processing of step S95, the processing proceeds to step S97. In step S97, the evaluation value determination unit 173 determines whether or not there is an edge between the evaluation frames 2 and 4 on the basis of the calculation results of the evaluation values of the evaluation frames 2 and 4.

In a case where it is determined as affirmative in the determination processing of step S97, the processing proceeds to step S98. In step S98, the evaluation result setting unit 174 sets the Y direction end position of the evaluation frame 2 as the mask diameter edge upper end position.

Furthermore, in a case where it is determined as negative in the determination processing of step S97, the processing proceeds to step S99. In step S99, the evaluation result setting unit 174 sets the Y direction end position of the evaluation frame 4 as the mask diameter edge upper end position.

Figure 16:
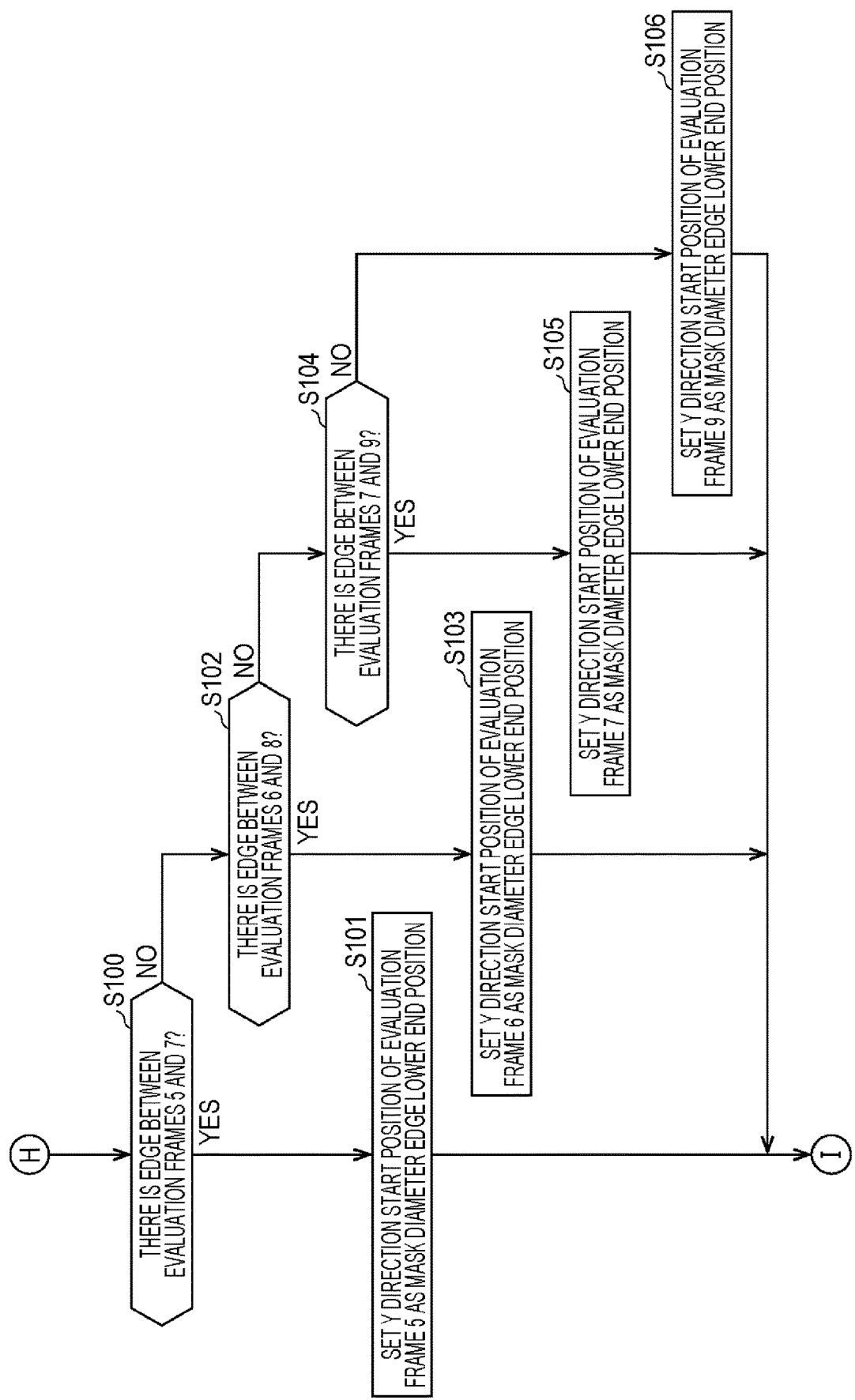
FIG. 16 is a flowchart explaining the flow of the fifth processing.

When the mask diameter edge upper end position is set in the processing of step S94, S96, S98, or S99, the processing proceeds to step S100 of FIG. 16.

In step S100, the evaluation value determination unit 173 determines whether or not there is an edge between the evaluation frames 5 and 7 on the basis of the calculation results of the evaluation values of the evaluation frames 5 and 7.

In a case where it is determined as affirmative in the determination processing of step S100, the processing proceeds to step S101. In step S101, the evaluation result setting unit 174 sets the Y direction start position of the evaluation frame 5 as the mask diameter edge lower end position.

Furthermore, in a case where it is determined as negative in the determination processing of step S100, the processing proceeds to step S102. In step S102, the evaluation value determination unit 173 determines whether or not there is an edge between the evaluation frames 6 and 8 on the basis of the calculation results of the evaluation values of the evaluation frames 6 and 8.

In a case where it is determined as affirmative in the determination processing of step S102, the processing proceeds to step S103. In step S103, the evaluation result setting unit 174 sets the Y direction start position of the evaluation frame 6 as the mask diameter edge lower end position.

Furthermore, in a case where it is determined as negative in the determination processing of step S102, the processing proceeds to step S104. In step S104, the evaluation value determination unit 173 determines whether or not there is an edge between the evaluation frames 7 and 9 on the basis of the calculation results of the evaluation values of the evaluation frames 7 and 9.

In a case where it is determined as affirmative in the determination processing of step S104, the processing proceeds to step S105. In step S105, the evaluation result setting unit 174 sets the Y direction start position of the evaluation frame 7 as the mask diameter edge lower end position.

Furthermore, in a case where it is determined as negative in the determination processing of step S104, the processing proceeds to step S106. In step S106, the evaluation result setting unit 174 sets the Y direction start position of the evaluation frame 9 as the mask diameter edge lower end position.

When the mask diameter edge lower end position is set in the processing of step S101, S103, S105, or S106, in the CCU 51, determination processing is executed following the fifth processing. Note that, details of the determination processing will be described later with reference to FIG. 18 and the like.

The flow of the fifth processing has been described above. In the fifth processing, a processing for calculating a detailed mask edge in the vertical direction (Y direction) is performed depending on the evaluation results in the second processing and the third processing described above, and as illustrated in FIG. 17, the evaluation frames 210-0 to 210-4 and the evaluation frames 210-5 to 210-9 are continuously arranged in vertical symmetry in the vertical direction for the endoscopic image 200, and the edge upper end position and the edge lower end position in the mask diameter are set on the basis of the relationship (correlation) between the evaluation values regarding the respective evaluation frames 210.

As described above, in a case where the operation is performed in the high accuracy calculation mode, the mask type of the mask area included in the endoscopic image 200 is set on the basis of the relevance of the evaluation values corresponding to the respective plurality of evaluation frames 210 by the first processing to the fifth processing, and each of the edge left end position, the edge right end position, the edge upper end position, and the edge lower end position is set in the mask diameter corresponding to the mask type. For example, in a case where a range of an allowable error is narrow, or the like, it is necessary to obtain the mask diameter and the center position more accurately, and in that case, the high accuracy calculation mode is set as the operation mode. Thus, a position of a vignetting area in the endoscope image, which depends on how the scope is attached, as well as a mask diameter may be estimated.

Note that, in the fourth processing and the fifth processing described above, a case has been described where the plurality of evaluation frames 210 is continuously arranged to be point-symmetrical with respect to the approximate center of gravity of the endoscopic image 200; however, similarly to the second processing and the third processing, the plurality of evaluation frames 210 may be discretely arranged at a predetermined interval. Furthermore, the number of the plurality of evaluation frames 210 continuously arranged is not limited to five, and may be four or less, or six or more. Moreover, the shape of each of the plurality of evaluation frames 210 continuously arranged is not limited to a rectangle, and may be another shape, and it is not necessary that all the evaluation frames 210 have the same shape.

Moreover, in the fourth processing and the fifth processing, an example has been described in which an edge (mask edge 220) is detected by using a luminance value as an evaluation value and comparing a luminance difference with a predetermined threshold value; however, the edge may be detected by using, as the evaluation value, a quantitative value (for example, a feature value such as an edge amount or a black area amount) representing an edge, a black area, or the like included in the frame 210.

(Flow of Determination Processing)

Figure 18:
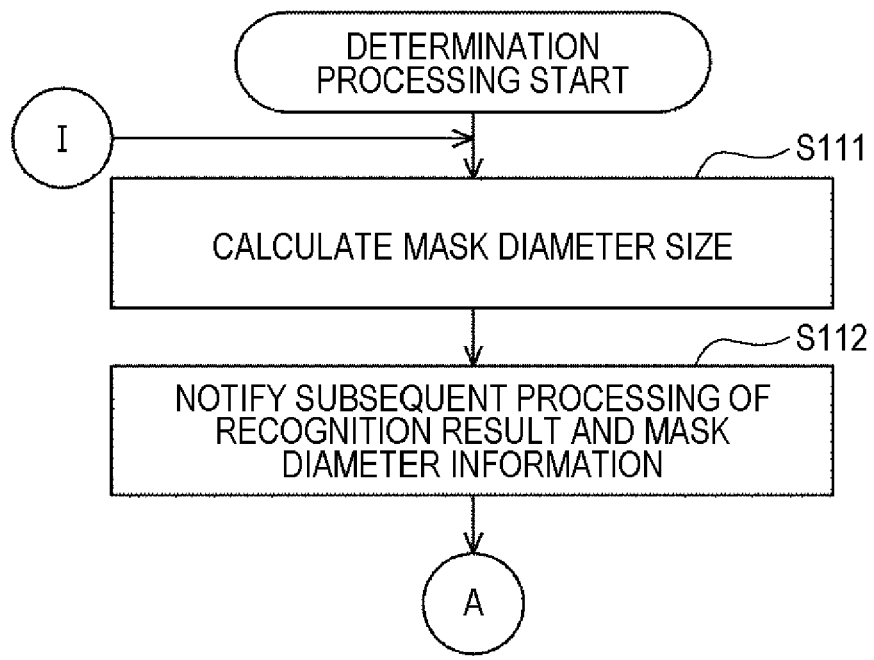
FIG. 18 is a flowchart explaining a flow of determination processing.

Next, a flow of determination processing executed by the CCU 51 will be described with reference to a flowchart of FIG. 18.

In step S111, the type estimation unit 175 calculates a mask diameter size on the basis of the processing results of the above-described first processing to fifth processing.

For example, in a case where the operation is performed in the high accuracy calculation mode, since the mask diameter edge left end position, edge right end position, edge upper end position, and edge lower end position each are set, by using these edge positions, the mask diameter and the mask center position can be obtained.

Figure 19:
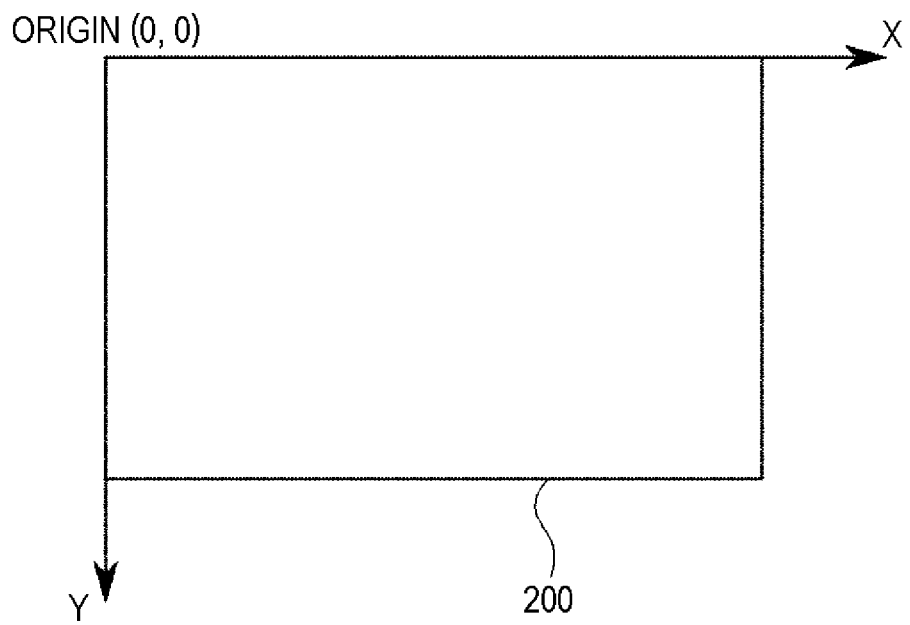
FIG. 19 is a diagram illustrating an example of a coordinate system of the evaluation frames.

Specifically, diameters in the horizontal and vertical directions of the mask are obtained by, for example, the following equations (3) and (4). However, coordinates of the evaluation frame 210 is represented by an orthogonal coordinate system in which the X-axis in the horizontal direction and the Y-axis in the vertical direction are orthogonal to each other, and as illustrated in FIG. 19, the position of the upper left vertex of the endoscopic image 200 is the origin (0, 0).

Mask diameter (horizontal direction)=edge right end position−edge left end position  (3)

Mask diameter (vertical direction)=edge lower end position−edge upper end position  (4)

Furthermore, the center position (x, y) in the horizontal and vertical directions of the mask is obtained by, for example, the following equations (5) and (6). However, here too, the coordinates of the evaluation frame 210 are represented by the orthogonal coordinate system illustrated in FIG. 19.

$$x=(\text{edge right end position}-\text{edge left end position})/2+\text{edge left end position} \quad (5)$$

$$y=(\text{edge lower end position}-\text{edge upper end position})/2+\text{edge upper end position} \quad (6)$$

As described above, in the type estimation unit 175, the mask diameter size included in the endoscopic image 200 is calculated, and the mask diameter has high relevance to the type of the scope 101. It can therefore also be said that the type estimation unit 175 estimates the diameter of the scope 101 by calculating the mask diameter size. Then, by estimating the diameter of the scope 101, the type of the scope 101 used in the endoscope 10 can be determined. In other words, it can also be said that the type of the scope 101 is determined by the diameter of the scope 101.

When the mask diameter size is calculated in the processing of step S111, the processing proceeds to step S112. Then, in the CCU 51, the subsequent processing is notified of the recognition results obtained in the above-described first processing to the fifth processing, and mask diameter information obtained in the processing of step S111. However, the mask diameter information can include information regarding the mask center position in addition to the mask diameter.

Here, the subsequent processing includes, for example, signal processing such as Autofocus (AF), Automatic Exposure (AE), Auto White Balance (AWB), and Expanded Depth of Field (EDOF).

As described above, for example, the endoscopic image 200 includes the mask area (black area) depending on the diameter of the scope 101 in addition to the area of the subject image, and when signal processing regarding AF, AE, or the like is performed, various problems arise when focusing or exposing is performed including the mask area. On the other hand, in the present technology, since the type of the scope 101 used can be reliably determined with a smaller amount of calculation, signal processing is performed on the area of the subject image, and AF, AE, or the like with higher accuracy can be realized.

Furthermore, for example, in signal processing regarding EDOF (for example, processing for expanding the depth of field), the mask center position is an important parameter, and the operation is performed in the high accuracy calculation mode, whereby a mask center position with higher accuracy is calculated and the accuracy of signal processing regarding EDOF can be improved.

The flow of the determination processing has been described above. In the determination processing, in a case where the operation is performed in the high accuracy calculation mode, the type of the scope 101 can be determined by calculating the diameter and center position of the mask and estimating the diameter and center position of the scope 101, with a smaller amount of calculation and higher accuracy, on the basis of the edge left end position, edge right end position, edge upper end position, and edge lower end position in the mask diameter corresponding to the mask type.

As described above, in a case where the operation is performed in the normal mode as the operation mode, the second processing and the third processing are executed, and the mask type is set on the basis of the relevance of the evaluation values corresponding to the respective plurality of evaluation frames 210, and the mask diameter size corresponding to the mask type is obtained, whereby the type (diameter) of the scope 101 is estimated.

Furthermore, in a case where the operation is performed in the high accuracy calculation mode as the operation mode, the fourth processing and the fifth processing are executed in addition to the second processing and the third processing, and the edge left end position, edge right end position, edge upper end position, and edge lower end position in the mask diameter corresponding to the mask type are calculated on the basis of the relevance of the evaluation values corresponding to the respective plurality of evaluation frames 210, and the mask diameter size is obtained on the basis of these types of position information (coordinates), whereby the type (diameter) of the scope 101 is estimated.

As described above, in both the normal mode and the high accuracy calculation mode, since the mask diameter size is obtained on the basis of the relevance (correlation) of the evaluation values corresponding to the respective plurality of evaluation frames 210 provided in the image, it is not necessary to perform processing for detecting all the straight edges in the image as disclosed in PTL 1 described above, and as a result, the type of the scope 101 can be determined with a smaller amount of calculation.

2. Modifications

Note that, in the above, the description has been made assuming that the first processing to the fifth processing and the determination processing are executed by (the control unit 161 of) the CCU 51; however, those types of processing may be executed by another processing unit other than the CCU 51 in the endoscopic surgical system 1. In this case, the evaluation frame setting unit 171 to the type estimation unit 175 are provided in the other processing unit. Furthermore, among the evaluation frame setting unit 171 to the type estimation unit 175, some blocks may be provided in the control unit 161, and other blocks may be provided in the other processing unit.

Furthermore, in the above description, the image signal corresponding to 4K resolution has been described as an image signal output from the camera head 102; however, this is not a limitation, and the image signal may be an image signal corresponding to another resolution, for example, 8K resolution (for example, 7680×4320 pixels), 2K resolution (for example, 1280×720 pixels), or the like.

In the above description, the mask diameter information is generated to determine the type of the scope 101, and then the subsequent signal processing is performed. However, parameters corresponding to the type of the scope 101 may be read to determine the type of the scope 101. For example, a table in which mask diameter information is linked with parameters necessary for signal processing may be stored in advance, and the parameters for signal processing corresponding to the type of the scope 101 may be read on the basis of the mask diameter information.

Furthermore, in the above description, a case has been described where the plurality of evaluation frames 210 is arranged at positions in two directions of the vertical and horizontal directions; however, not limited to the positions in the vertical and horizontal directions, the plurality of evaluation frames 210 may be arranged at any positions as long as the mask diameter can be detected. Furthermore, regarding the size of the evaluation frame 210, it is not necessary that all the evaluation frames 210 have the same size, and for example, the size of the evaluation frame 210 may vary depending on the arrangement position. Furthermore, the intervals of the plurality of evaluation frames 210 arranged at predetermined intervals are not limited to the same intervals, and may be different intervals.

Note that, in the above description, for convenience of description, an image corresponding to the imaging surface of the imaging element of the camera head 102 is referred to as an endoscopic image; however, while an image corresponding to the subject image focused by the scope 101 may be referred to as an endoscopic image, an image corresponding to the imaging surface of the imaging element of the camera head 102 may be referred to as an observation image and distinguished. In this case, the observation image includes the endoscopic image, a plurality of evaluation frames is set at a predetermined interval for the observation image, evaluation values regarding the respective plurality of evaluation frames set are calculated, and a mask diameter size corresponding to the endoscopic image is calculated on the basis of the relationship between the evaluation values calculated.

3. Configuration of Computer

Figure 20:
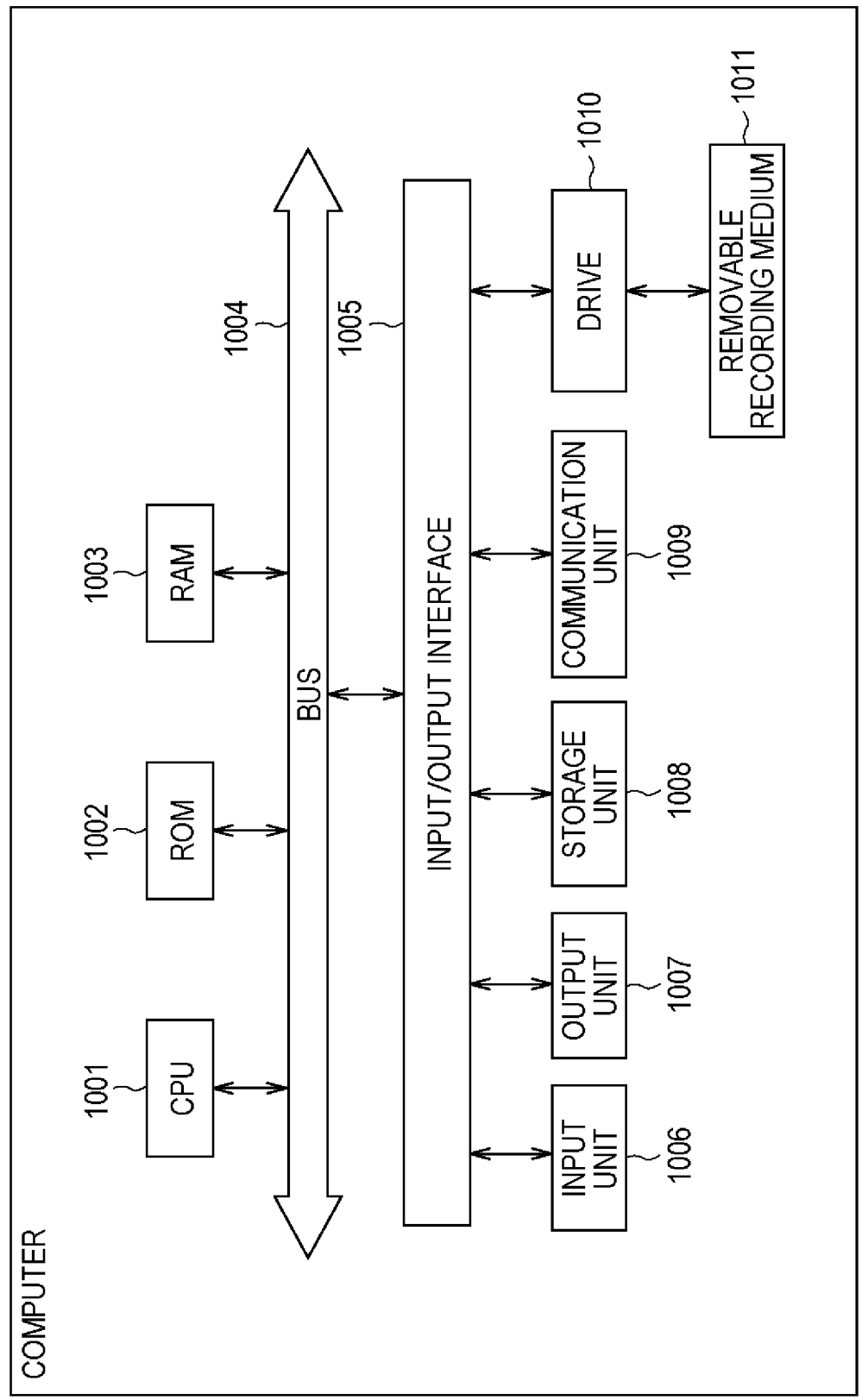
FIG. 20 is a diagram illustrating an example of a configuration of a computer.

A series of processing steps described above (for example, the first processing to the fifth processing and the determination processing described above) can be executed by hardware, or can be executed by software. In a case where the series of processing steps is executed by software, a program constituting the software is installed in a computer of each device. As used herein 'computer' refers to circuitry that may be configured via the execution of computer readable instructions, and the circuitry may include one or more local processors (e.g., CPU's), and/or one or more remote processors, such as a cloud computing resource, or any combination thereof. For example, the present technology can be configured as a form of cloud computing in which one function is shared in cooperation for processing among a plurality of devices via a network. Also, the present technology can be configured as a form of a server or IP converter in a hospital in which one function is shared in cooperation for processing among a plurality of devices via a network. FIG. 20 is a block diagram illustrating a configuration example of hardware of the computer that executes the above-described series of processing steps by the program.

In the computer, a central processing unit (CPU) 1001, a read only memory (ROM) 1002, and a random access memory (RAM) 1003 are connected to each other by a bus 1004. Moreover, an input/output interface 1005 is connected to the bus 1004. The input/output interface 1005 is connected to an input unit 1006, an output unit 1007, a storage unit 1008, a communication unit 1009, and a drive 1010.

The input unit 1006 includes a microphone, a keyboard, a mouse, and the like. The output unit 1007 includes a speaker, a display, and the like. The storage unit 1008 includes a hard disk, a nonvolatile memory, or the like. The communication unit 1009 includes a network interface and the like. The drive 1010 drives a removable recording medium 1011 such as a magnetic disk, an optical disk, a magneto-optical disk, or a semiconductor memory.

In the computer configured as described above, the CPU 1001 loads and executes the program recorded in the ROM 1002 or the storage unit 1008 to the RAM 1003 via the input/output interface 1005 and the bus 1004, whereby the above-described series of processing steps is performed.

The program executed by the computer (CPU 1001) can be provided, for example, by being recorded in the removable recording medium 1011 as a package medium or the like. Furthermore, the program can be provided via a wired or wireless transmission medium such as a local area network, the Internet, or digital satellite broadcasting.

In the computer, the program can be installed to the storage unit 1008 via the input/output interface 1005 by mounting the removable recording medium 1011 to the drive 1010. Furthermore, the program can be installed to the storage unit 1008 by receiving with the communication unit 1009 via the wired or wireless transmission medium. In addition, the program can be installed in advance to the ROM 1002 or the storage unit 1008.

Here, in the present specification, the processing performed by the computer in accordance with the program does not necessarily have to be performed chronologically in the order described as the flowchart. In other words, the processing performed by the computer in accordance with the program also includes processing executed in parallel or individually (for example, parallel processing or processing by an object). Furthermore, the program may be processed by one computer (processor) or may be distributed and processed by a plurality of computers.

Note that, the embodiment of the present technology is not limited to the embodiments described above, and various modifications are possible without departing from the scope of the present technology.

Furthermore, the present technology can have a configuration as follows.

(1)
An image processing system including
a control unit that
sets a plurality of evaluation frames arranged at a predetermined interval for an endoscopic image captured by using a scope,
calculates evaluation values regarding the respective plurality of evaluation frames set, and
estimates a type of the scope on the basis of a relationship between the evaluation values calculated.

(2)
The image processing system according to (1), in which the control unit discretely arranges the plurality of evaluation frames at the predetermined interval.

(3)
The image processing system according to (1) or (2), in which
the control unit sets the predetermined interval such that the plurality of evaluation frames is point-symmetrical with respect to an approximate center of gravity of the endoscopic image.

(4)
The image processing system according to any of (1) to (3), in which
the control unit does not make the predetermined interval constant.

(5)
The image processing system according to any of (1) to (4), in which
the type of the scope is determined by a diameter of the scope.

(6)
The image processing system according to (2), in which the control unit
discretely arranges the plurality of evaluation frames in a case where the type of the scope is estimated in a first mode, and continuously arranges the plurality of evaluation frames in a case where the type of the scope is estimated in a second mode in which accuracy is higher than in the first mode.

(7)
The image processing system according to (6), in which
the control unit positions the plurality of evaluation frames continuously arranged, on the basis of evaluation results of the evaluation values corresponding to the respective plurality of evaluation frames discretely arranged.

(8)
The image processing system according to any of (1) to (7), in which
the control unit estimates the type of the scope from a difference between the evaluation values corresponding to respective evaluation frames arranged adjacent to each other or at a constant interval, among the plurality of evaluation frames.

(9)
The image processing system according to any of (1) to (8), in which
the control unit estimates the type of the scope and a center position of the scope.

(10)
The image processing system according to any of (6) to (9), in which
the control unit makes sizes of the respective plurality of evaluation frames continuously arranged smaller than sizes of the respective plurality of evaluation frames discretely arranged.

(11)
The image processing system according to any of (1) to (10), in which p1 the control unit
arranges the plurality of evaluation frames in each of a horizontal direction and a vertical direction for the endoscopic image, and
calculates the evaluation values from feature values detected from respective areas corresponding to the respective plurality of evaluation frames for the endoscopic image, for each of the horizontal direction and the vertical direction.

(12)
The image processing system according to (11), in which the feature values include a luminance value.

(13)
The image processing system according to (11), in which the feature values include an edge amount or a black area amount.

(14)
The image processing system according to any of (11) to (13), in which
the control unit arranges the plurality of evaluation frames substantially symmetrically about an approximate center of gravity of the endoscopic image.

(15)
The image processing system according to any of (1) to (14), in which
the control unit
arranges the plurality of evaluation frames near an approximate center of gravity and vertex of the endoscopic image,
calculates the evaluation values from feature values detected from areas corresponding to the respective plurality of evaluation frames for the endoscopic image, and
determines whether or not a mask area is included in the endoscopic image on the basis of the evaluation values calculated.

(16)
The image processing system according to any of (1) to (15), in which
on the basis of information corresponding to the type of the scope estimated, among pieces of signal processing regarding Autofocus (AF), Automatic Exposure (AE), Auto White Balance (AWB), and Expanded Depth of Field (EDOF), at least one of the pieces of signal processing is performed.

(17)
The image processing system according to any of (1) to (16), in which
the scope is configured as part of an endoscope.

(18)
An image processing device including
a control unit that
sets a plurality of evaluation frames arranged at a predetermined interval for an endoscopic image captured by using a scope,
calculates evaluation values regarding the respective plurality of evaluation frames set, and
performs signal processing corresponding to a type of the scope on the basis of a relationship between the evaluation values calculated.

(19)
The image processing device according to (18), in which
the control unit
discretely arranges the plurality of evaluation frames in a case where the type of the scope is estimated in a first mode, and
continuously arranges the plurality of evaluation frames on the basis of evaluation results of the evaluation values corresponding to the respective plurality of evaluation frames discretely arranged in a case where the type of the scope is estimated in a second mode in which accuracy is higher than in the first mode.

(20)
An image processing method including,
by an image processing device,
setting a plurality of evaluation frames arranged at a predetermined interval for an endoscopic image captured by using a scope,
calculating evaluation values regarding the respective plurality of evaluation frames set, and
performing signal processing corresponding to a type of the scope on the basis of a relationship between the evaluation values calculated.

(21)
An endoscope system including:
circuitry configured to:
set a plurality of evaluation areas in an endoscope image captured by an image sensor via a scope, adjacent ones of the plurality of evaluation areas being spatially separated from one another;
calculate an evaluation value for each of the plurality of evaluation areas;
compare an evaluation value of the plurality of evaluation areas; and
adjust an image processing on the endoscope image in accordance with a result of the comparison.

(22)
The endoscope system according to (21), wherein
the plurality of evaluation areas is discretely set at a predetermined interval.

(23)

The endoscope system according to any of (21) and (22), wherein
the plurality of evaluation areas is set such that the plurality of evaluation areas is point-symmetrical with respect to an approximate center of gravity of the endoscope image.

(24)

The endoscope system according to (22), wherein
the predetermined interval of the plurality of evaluation areas is not constant.

(25)

The endoscope system according to any of (21) to (24), wherein
the circuitry configured to estimate a type of a scope based on the comparison and adjust the image processing on the endoscope image based on the type of the scope.

(26)

The endoscope system according to (25), wherein
the circuitry is configured to recognize a presence of a scope and to estimate, when present, to estimate the type of the scope is based on a size of an area of the endoscope image.

(27)

The endoscope system according to any of (21) to (26), wherein
the circuitry configured to
set the plurality of evaluation areas, adjacent ones of the plurality of evaluation areas being spatially separated and discrete from one another in a first mode;
set the plurality of evaluation areas, adjacent ones of the plurality of evaluation areas being spatially separated and continuous from one another in a second mode.

(28)

The endoscope system according to (27), wherein
the circuitry configured to estimate the type of the scope based on the comparison in the first mode and estimate a position of a vignetting area in the endoscope image based on the comparison in the second mode.

(29)

The endoscope system according to (27), wherein
the plurality of evaluation areas in the second mode is set at predetermined positions based on the comparison of the first mode.

(30)

The endoscope system according to (27), wherein
sizes of the plurality of evaluation areas in the second mode is smaller than sizes of the plurality of evaluation areas in the first mode.

(31)

The endoscope system according to any of (21) to (30), wherein
the comparison is obtained from a difference between the evaluation values of adjacent areas of the plurality of evaluation areas.

(32)

The endoscope system according to any of (21) to (31), wherein
the circuitry is configured to
set the plurality of evaluation frames in each of a horizontal direction and a vertical direction for the endoscopic image;
compare an evaluation value of the plurality of evaluation areas of the horizontal direction;
compare an evaluation value of the plurality of evaluation areas of the vertical direction; and
adjust the image processing on the endoscope image in accordance with a result of the comparison of the horizontal direction and the comparison of the vertical direction.

(33)

The endoscope system according to any of (21) to (32), wherein
the evaluation value is calculated based on a luminance value of each the plurality of evaluation areas.

(34)

The endoscope system according to any of (21) to (33), wherein
the plurality of evaluation areas is set a center area of the endoscope image and the substantially symmetrically areas about the center area.

(35)

The endoscope system according to (34), wherein
the circuitry configured to estimate whether the scope is attached based on the evaluation value of the center area and estimate the type of scope based on the comparison of the evaluation value of the substantially symmetrically areas about the center area.

(36)

The endoscope system according to any of (21) to (35), wherein
an image processing is at least one of auto-focus processing, auto-exposure processing, auto-white balance processing, or expanded depth of field processing.

(37)

The endoscope system according to any of (21) to (36), wherein
the circuitry is configured to estimate the type of the scope by determining a position of an edge of vignetting caused by the scope based on the comparison.

(38)

The endoscope system according to any of (21) to (37), wherein
the circuitry is configured to read a parameter from a table stored in a memory based on the comparison the comparison and to adjust the image processing using the parameter.

(39)

A non-transitory computer readable medium having stored thereon a program that, when executed by a computer, causes the computer to execute processing, the processing including:
setting a plurality of evaluation areas in an endoscope image captured by an image sensor via a scope, adjacent ones of the plurality of evaluation areas being spatially separated from one another;
calculating an evaluation value for each of the plurality of evaluation areas;
comparing an evaluation value of the plurality of evaluation areas; and
adjusting an image processing on the endoscope image in accordance with a result of the comparison.

(40)

A method, including:
setting a plurality of evaluation areas in an endoscope image captured by an image sensor via a scope, adjacent ones of the plurality of evaluation areas being spatially separated from one another;
calculating an evaluation value for each of the plurality of evaluation areas;
comparing an evaluation value of the plurality of evaluation areas; and adjusting an image processing on the endoscope image in accordance with a result of the comparison.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

1 Endoscopic surgical system
10 Endoscope
20 Surgical instrument
30 Support arm device
51 CCU
52 Display device
53 Light source device
54 Input device
55 Treatment tool control device
56 Pneumoperitoneum device
57 Recorder
58 Printer
101 Scope
102 Camera head
151 Lens unit
152 Imaging unit
153 Drive unit
154 Communication unit
155 Camera head control unit
161 Control unit
162 Communication unit
163 Image processing unit
171 Evaluation frame setting unit
172 Evaluation value calculation unit
173 Evaluation value determination unit
174 Evaluation result setting unit
175 Type estimation unit
1001 CPU

The invention claimed is:

1. An endoscope system comprising:
circuitry configured to:
set a plurality of discrete evaluation areas in an endoscope image captured by an image sensor via a scope, adjacent ones of the plurality of discrete evaluation areas being spatially separated from one another;
calculate an evaluation value for each of the plurality of discrete evaluation areas;
estimate whether the scope is attached based on at least one evaluation value of the plurality of discrete evaluation areas; and
estimate the type of scope based on comparison of at least two evaluation values of the plurality of discrete evaluation areas; and
adjust an image processing on the endoscope image in accordance with the type of scope estimated.

2. The endoscope system according to claim 1, wherein the plurality of discrete evaluation areas are spaced apart at a predetermined interval.

3. The endoscope system according to claim 2, wherein the predetermined interval of the plurality of discrete evaluation areas is not constant.

4. The endoscope system according to claim 1, wherein the plurality of discrete evaluation areas is set such that the plurality of discrete evaluation areas is point-symmetrical with respect to an approximate center of gravity of the endoscope image.

5. The endoscope system according to claim 1, wherein the circuitry configured to estimate a type of a scope based on the comparison and adjust the image processing on the endoscope image based on the type of the scope.

6. The endoscope system according to claim 5, wherein the circuitry is configured to recognize a presence of a scope and to estimate, when present, to estimate the type of the scope based on a size of an area of the endoscope image.

7. The endoscope system according to claim 1, wherein on condition that the image processing is adjusted to further process the endoscope image, the circuitry is configured to
set another plurality of discrete evaluation areas in a first mode; and
set a plurality of continuous evaluation areas, adjacent ones of the plurality of continuous evaluation areas being spatially separated and continuous from one another in a second mode.

8. The endoscope system according to claim 7, wherein the circuitry configured to estimate the type of the scope based on the comparison in the first mode and estimate a position of a vignetting area in the endoscope image based on the comparison in the second mode.

9. The endoscope system according to claim 7, wherein the plurality of continuous evaluation areas in the second mode is set at predetermined positions based on the comparison of the first mode.

10. The endoscope system according to claim 7, wherein sizes of the plurality of continuous evaluation areas in the second mode is smaller than sizes of the another plurality of discrete evaluation areas in the first mode.

11. The endoscope system according to claim 1, wherein the comparison is obtained from a difference between the evaluation values of adjacent areas of the plurality of discrete evaluation areas.

12. The endoscope system according to claim 1, wherein the circuitry is configured to
set the plurality of discrete evaluation frames in each of a horizontal direction and a vertical direction for the endoscopic image;
compare an evaluation value of the plurality of discrete evaluation areas of the horizontal direction;
compare an evaluation value of the plurality of discrete evaluation areas of the vertical direction; and
adjust the image processing on the endoscope image in accordance with a result of the comparison of the horizontal direction and the comparison of the vertical direction.

13. The endoscope system according to claim 1, wherein the evaluation value is calculated based on a luminance value of each the plurality of discrete evaluation areas.

14. The endoscope system according to claim 1, wherein the at least one evaluation value is for a center area of the endoscope image and at least two evaluation values are for substantially symmetrically areas about the center area.

15. The endoscope system according to claim 1, wherein an image processing is at least one of auto-focus processing, auto-exposure processing, auto-white balance processing, or expanded depth of field processing.

16. The endoscope system according to claim 1, wherein the circuitry is configured to estimate the type of the scope by determining a position of an edge of vignetting caused by the scope based on the comparison.

17. The endoscope system according to claim 1, wherein the circuitry is configured to read a parameter from a table stored in a memory based on the comparison the comparison and to adjust the image processing using the parameter.

18. A non-transitory computer readable medium having stored thereon a program that, when executed by a computer, causes the computer to execute processing, the processing comprising:
setting a plurality of discrete evaluation areas in an endoscope image captured by an image sensor via a scope, adjacent ones of the plurality of discrete evaluation areas being spatially separated from one another;
calculating an evaluation value for each of the plurality of discrete evaluation areas;
estimating whether the scope is attached based on at least one evaluation value of the plurality of discrete evaluation areas;
estimating the type of scope based on comparison of at least two evaluation values of the plurality of discrete evaluation areas; and
adjusting an image processing on the endoscope image in accordance with the type of scope estimated.

19. A method, comprising:
setting a plurality of discrete evaluation areas in an endoscope image captured by an image sensor via a scope, adjacent ones of the plurality of discrete evaluation areas being spatially separated from one another, wherein the plurality of discrete evaluation areas includes a center area of the endoscope image and the substantially symmetrically areas about the center area;
calculating an evaluation value for each of the plurality of discrete evaluation areas,
estimating whether the scope is attached based on at least one evaluation value of the plurality of discrete evaluation areas;
estimating the type of scope based on comparison of at least two evaluation values of the plurality of discrete evaluation areas; and
adjusting an image processing on the endoscope image in accordance with the type of scope estimated.

* * * * *